(12) United States Patent
Edwards et al.

(10) Patent No.: US 10,667,859 B2
(45) Date of Patent: *Jun. 2, 2020

(54) REPLACABLE DEBRIDER BLADE MODULE WITH LATCHING MECHANISM

(71) Applicant: GYRUS ACMI, INC., Southborough, MA (US)

(72) Inventors: Kevin C. Edwards, Olive Branch, MS (US); Tomas Matusaitis, Chicago, IL (US); Sean Corrigan, Chicago, IL (US); Antonio J. Belton, Richton Park, IL (US)

(73) Assignee: Gyrus Acmi, Inc., Southborough, MA (US)

( * ) Notice: Subject to any disclaimer, the term of this patent is extended or adjusted under 35 U.S.C. 154(b) by 278 days.

This patent is subject to a terminal disclaimer.

(21) Appl. No.: 15/799,739

(22) Filed: Oct. 31, 2017

(65) Prior Publication Data

US 2018/0049797 A1  Feb. 22, 2018

Related U.S. Application Data

(63) Continuation of application No. 13/826,892, filed on Mar. 14, 2013, now Pat. No. 9,844,408.

(Continued)

(51) Int. Cl.
*A61B 18/14* (2006.01)
*A61B 17/32* (2006.01)
(Continued)

(52) U.S. Cl.
CPC ...... *A61B 18/149* (2013.01); *A61B 17/32002* (2013.01); *A61B 17/320016* (2013.01);
(Continued)

(58) Field of Classification Search
CPC ...... A61B 17/320016; A61B 17/32002; A61B 18/14; A61B 18/1402; A61B 18/1482; A61B 18/149
See application file for complete search history.

(56) References Cited

U.S. PATENT DOCUMENTS 3,223,088 A  12/1965  Barber et al.
3,955,284 A  5/1976  Balson
(Continued)

FOREIGN PATENT DOCUMENTS

AU  2013379686 B2  4/2018
AU  2013379687 B2  4/2018
(Continued)

OTHER PUBLICATIONS

PKS Cutting Forceps, General Surgery Products, Gyrus ACMI, An Olympus Company, available at www.gyrusacmi.com/user/display.cfm?display=product&pid=9063&catud=69&mainacat=General, last accessed and downloaded on Oct. 18, 2012.
(Continued)

*Primary Examiner* — Sarah A Simpson
(74) *Attorney, Agent, or Firm* — Schwegman Lundberg & Woessner, P.A.

(57) ABSTRACT

A blade assembly comprising: a tip including two or more tubes, wherein the two or more tubes include at least: an outer tube and an inner tube; and a mechanical enclosure including: a locking spline having a longitudinal axis; and a slide lock; wherein the slide lock slides along the longitudinal axis of the locking spline and over the locking spline forming a locked state so that rotational movement of the locking spline, around the longitudinal axis of the locking spline, is prevented; and wherein the outer tube is coupled to the locking spline so that rotational movement of the outer (Continued)

tube, around the longitudinal axis of the locking spline, is prevented during the locked state.

19 Claims, 12 Drawing Sheets

Related U.S. Application Data

(60) Provisional application No. 61/769,480, filed on Feb. 26, 2013, provisional application No. 61/731,919, filed on Nov. 30, 2012.

(51) Int. Cl.
    *A61B 90/90*     (2016.01)
    *A61B 34/20*     (2016.01)
    *A61B 90/98*     (2016.01)
    *A61B 18/12*     (2006.01)
    *A61B 17/00*     (2006.01)
    *A61B 18/00*     (2006.01)

(52) U.S. Cl.
    CPC .......... *A61B 18/1206* (2013.01); *A61B 18/14* (2013.01); *A61B 18/1402* (2013.01); *A61B 18/1482* (2013.01); *A61B 34/20* (2016.02); *A61B 90/90* (2016.02); *A61B 90/98* (2016.02); *A61B 2017/0046* (2013.01); *A61B 2017/00225* (2013.01); *A61B 2017/00464* (2013.01); *A61B 2017/00473* (2013.01); *A61B 2017/00482* (2013.01); *A61B 2017/00526* (2013.01); *A61B 2018/0019* (2013.01); *A61B 2018/0094* (2013.01); *A61B 2018/00178* (2013.01); *A61B 2018/00208* (2013.01); *A61B 2018/00708* (2013.01); *A61B 2018/00988* (2013.01); *A61B 2018/126* (2013.01); *A61B 2018/1253* (2013.01); *Y10T 29/49002* (2015.01); *Y10T 29/49169* (2015.01)

(56) References Cited

U.S. PATENT DOCUMENTS

| | | | |
|---|---|---|---|
| 4,014,342 A | 3/1977 | Staub et al. | |
| 4,878,493 A | 11/1989 | Pasternak et al. | |
| 5,112,299 A | 5/1992 | Pascaloff | |
| 5,230,704 A | 7/1993 | Moberg et al. | |
| 5,275,609 A | 1/1994 | Pingleton et al. | |
| 5,282,821 A * | 2/1994 | Donahue | A61B 17/1604 604/22 |
| 5,352,222 A | 10/1994 | Rydell et al. | |
| 5,376,078 A * | 12/1994 | Dinger, III | A61B 17/32002 604/22 |
| 5,395,312 A | 3/1995 | Desai | |
| 5,405,348 A | 4/1995 | Anspach et al. | |
| 5,413,556 A | 5/1995 | Whittingham | |
| 5,492,527 A | 2/1996 | Glowa et al. | |
| 5,540,708 A | 7/1996 | Lim et al. | |
| 5,560,373 A | 10/1996 | DeSantis | |
| 5,569,254 A | 10/1996 | Carlson et al. | |
| 5,601,583 A * | 2/1997 | Donahue | A61B 17/32002 604/22 |
| 5,609,573 A | 3/1997 | Sandock | |
| 5,620,415 A | 4/1997 | Lucey et al. | |
| 5,620,447 A | 4/1997 | Smith et al. | |
| 5,697,947 A | 12/1997 | Wolf et al. | |
| 5,712,543 A | 1/1998 | Sjostrom | |
| 5,792,167 A | 8/1998 | Kablik et al. | |
| 5,810,809 A | 9/1998 | Rydell | |
| 5,814,044 A | 9/1998 | Hooven | |
| 5,833,692 A | 11/1998 | Cesarini et al. | |
| 5,849,023 A | 12/1998 | Mericle | |
| 5,873,886 A | 2/1999 | Larsen et al. | |
| 5,899,915 A | 5/1999 | Saadat | |
| 5,904,681 A | 5/1999 | West, Jr. | |
| 5,976,164 A | 11/1999 | Bencini et al. | |
| 6,001,096 A | 12/1999 | Bissinger et al. | |
| 6,010,476 A | 1/2000 | Saadat | |
| 6,042,593 A | 3/2000 | Storz et al. | |
| 6,053,923 A | 4/2000 | Veca et al. | |
| 6,074,386 A | 6/2000 | Goble et al. | |
| 6,152,941 A | 11/2000 | Himes et al. | |
| 6,217,598 B1 | 4/2001 | Berman et al. | |
| 6,221,088 B1 | 4/2001 | Bays | |
| 6,246,638 B1 | 6/2001 | Zook et al. | |
| 6,293,957 B1 | 9/2001 | Peters et al. | |
| 6,296,638 B1 | 10/2001 | Davison et al. | |
| 6,454,782 B1 | 9/2002 | Schwemberger | |
| 6,494,892 B1 | 12/2002 | Ireland et al. | |
| 6,716,215 B1 | 4/2004 | David et al. | |
| 6,752,816 B2 | 6/2004 | Culp et al. | |
| 6,824,550 B1 | 11/2004 | Noriega et al. | |
| 6,979,332 B2 | 12/2005 | Adams | |
| 7,179,255 B2 | 2/2007 | Lettice et al. | |
| 7,237,990 B2 | 7/2007 | Deng | |
| 7,247,161 B2 | 7/2007 | Johnston et al. | |
| 7,276,074 B2 | 10/2007 | Adams et al. | |
| 7,416,539 B2 | 8/2008 | Johnston et al. | |
| 7,442,191 B2 | 10/2008 | Hovda et al. | |
| 7,608,048 B2 | 10/2009 | Goldenberg | |
| 7,674,263 B2 | 3/2010 | Ryan | |
| 8,109,956 B2 | 2/2012 | Shadeck | |
| 8,202,288 B2 | 6/2012 | Adams et al. | |
| 8,628,545 B2 | 1/2014 | Cabrera et al. | |
| 8,920,419 B2 | 12/2014 | Edwards et al. | |
| 8,956,355 B2 | 2/2015 | Edwards et al. | |
| 9,131,979 B2 | 9/2015 | Edwards et al. | |
| 9,844,408 B2 * | 12/2017 | Edwards | A61B 90/90 |
| 2001/0047183 A1 | 11/2001 | Privitera et al. | |
| 2002/0038129 A1 | 3/2002 | Peters et al. | |
| 2002/0165549 A1 | 11/2002 | Owusu-Akyaw et al. | |
| 2003/0093103 A1 | 5/2003 | Malackowski et al. | |
| 2003/0097129 A1 | 5/2003 | Davison et al. | |
| 2003/0165794 A1 | 9/2003 | Matoba | |
| 2004/0010258 A1 | 1/2004 | Quick et al. | |
| 2004/0167427 A1 | 8/2004 | Quick et al. | |
| 2004/0243163 A1 | 12/2004 | Casiano et al. | |
| 2005/0054947 A1 | 3/2005 | Goldenberg | |
| 2005/0222566 A1 | 10/2005 | Nakahira | |
| 2005/0277970 A1 * | 12/2005 | Norman | A61B 17/32002 606/180 |
| 2006/0259055 A1 | 11/2006 | Thorne et al. | |
| 2009/0270896 A1 | 10/2009 | Sullivan et al. | |
| 2010/0298763 A1 | 11/2010 | Adams et al. | |
| 2010/0317998 A1 | 12/2010 | Hibner et al. | |
| 2011/0009856 A1 | 1/2011 | Jorgensen et al. | |
| 2011/0017801 A1 | 1/2011 | Zemlok et al. | |
| 2011/0066142 A1 | 3/2011 | Tal et al. | |
| 2011/0301578 A1 | 12/2011 | Muniz-Medina et al. | |
| 2012/0109130 A1 | 5/2012 | Casey et al. | |
| 2012/0191117 A1 | 7/2012 | Palmer et al. | |
| 2012/0221035 A1 | 8/2012 | Harvey | |
| 2013/0004595 A1 | 1/2013 | Bhatia | |
| 2013/0310864 A1 | 11/2013 | Jezierski et al. | |
| 2014/0155888 A1 | 6/2014 | Edwards et al. | |
| 2014/0155889 A1 | 6/2014 | Edwards et al. | |
| 2014/0155923 A1 | 6/2014 | Edwards et al. | |
| 2014/0277036 A1 | 9/2014 | Flynn et al. | |
| 2015/0112334 A1 | 4/2015 | Edwards et al. | |

FOREIGN PATENT DOCUMENTS

| | | |
|---|---|---|
| CN | 1209047 A | 2/1999 |
| CN | 101011274 A | 8/2007 |
| CN | 101138483 A | 3/2008 |
| CN | 101167658 A | 4/2008 |
| CN | 101612053 A | 12/2009 |
| CN | 104684501 A | 6/2015 |
| CN | 104902829 A | 9/2015 |
| CN | 104902829 B | 5/2017 |
| CN | 107252340 A | 10/2017 |
| CN | 104684501 B | 11/2017 |

(56) References Cited

FOREIGN PATENT DOCUMENTS

| | | |
|---|---|---|
| EP | 1082944 A1 | 3/2001 |
| EP | 1201196 A1 | 5/2002 |
| EP | 1424944 A2 | 6/2004 |
| EP | 2044893 A2 | 4/2009 |
| EP | 2133028 A2 | 12/2009 |
| EP | 2882364 A1 | 6/2015 |
| EP | 2919678 A1 | 9/2015 |
| EP | 2919678 B1 | 3/2017 |
| EP | 2882364 B1 | 7/2018 |
| EP | 3378428 A1 | 9/2018 |
| GB | 2470607 A | 12/2010 |
| JP | H04158856 A | 6/1992 |
| JP | H06269459 A | 9/1994 |
| JP | H09327465 A | 12/1997 |
| JP | H11333875 A | 12/1999 |
| JP | 2000502578 A | 3/2000 |
| JP | 2002035009 A | 2/2002 |
| JP | 2003210480 A | 7/2003 |
| JP | 2004537367 A | 12/2004 |
| JP | 2008528223 A | 7/2008 |
| JP | 2008253464 A | 10/2008 |
| JP | 2009082705 A | 4/2009 |
| JP | 2009153989 A | 7/2009 |
| JP | 2012519023 A | 8/2012 |
| JP | 2016503680 A | 2/2016 |
| JP | 2016182521 A | 10/2016 |
| JP | 6043439 B2 | 12/2016 |
| JP | 6110514 B2 | 3/2017 |
| JP | 6407213 B2 | 9/2018 |
| WO | 96/37156 A1 | 11/1996 |
| WO | 97/23169 A1 | 7/1997 |
| WO | WO-9724073 A1 | 7/1997 |
| WO | 98/38932 A1 | 9/1998 |
| WO | WO-03013372 A2 | 2/2003 |
| WO | WO-2009142971 A1 | 11/2009 |
| WO | WO-2014133664 A1 | 9/2014 |

OTHER PUBLICATIONS

Gyrus ACMI; Handpiece Cleaning and Maintenance Jun. 1, 2006.
Potentially Related U.S. Appl. No. 13/804,308, filed Mar. 14, 2013.
Potentially Related U.S. Appl. No. 13/803,380, filed Mar. 14, 2013.
Potentially Related Patent U.S. Appl. No. 13/796,416, filed Mar. 12, 2013.
International Search Report and Written Opinion for Application No. PCT/US2013/077759 dated Jun. 18, 2014.
EPO Office Action for Application No. 13824063.5 dated Nov. 10, 2015.
Japanese Office Action for Application No. 2015-559235, dated Aug. 2, 2016.
Chinese Office Action for Application No. 201380069712.2 dated Sep. 1, 2016.
"U.S. Appl. No. 13/803,380, Examiner Interview Summary dated Oct. 21, 2014", 3 pgs.
"U.S. Appl. No. 13/803,380, Non Final Office Action dated Oct. 3, 2014", 7 pgs.
"U.S. Appl. No. 13/803,380, Notice of Allowance dated Nov. 5, 2014", 5 pgs.
"U.S. Appl. No. 13/803,380, Response filed Oct. 27, 2014 to Non Final Office Action dated Oct. 3, 2014", 10 pgs.
"U.S. Appl. No. 13/804,308, Notice of Allowance dated Aug. 27, 2014", 7 pgs.
"U.S. Appl. No. 13/804,308, Preliminary Amendment filed Feb. 12, 2014", 6 pgs.
"U.S. Appl. No. 13/804,308, Preliminary Amendment filed Apr. 18, 2014", 3 pgs.
"U.S. Appl. No. 13/826,892, Examiner Interview Summary dated Jun. 19, 2017", 3 pgs.
"U.S. Appl. No. 13/826,892, Final Office Action dated May 18, 2017", 17 pgs.
"U.S. Appl. No. 13/826,892, Non Final Office Action dated Sep. 15, 2016", 13 pgs.
"U.S. Appl. No. 13/826,892, Notice of Allowance dated Aug. 16, 2017", 11 pgs.
"U.S. Appl. No. 13/826,892, Response filed Jun. 14, 2017 to Final Office Action dated May 18, 2017", 9 pgs.
"U.S. Appl. No. 13/826,892, Response filed Dec. 9, 2016 to Non Final Office Action dated Sep. 15, 2016", 12 pgs.
"U.S. Appl. No. 14/583,977, Examiner Interview Summary dated May 12, 2015", 3 pgs.
"U.S. Appl. No. 14/583,977, Non Final Office Action dated Feb. 5, 2015", 7 pgs.
"U.S. Appl. No. 14/583,977, Notice of Allowance dated May 22, 2015", 5 pgs.
"U.S. Appl. No. 14/583,977, Preliminary Amendment filed Dec. 29, 2014", 6 pgs.
"U.S. Appl. No. 14/583,977, Response filed May 5, 2015 to Non Final Office Action dated Feb. 5, 2015", 10 pgs.
"Australian Application Serial No. 2013376987, Response filed Jan. 30, 2018 to Examination Report dated Aug. 3, 2017", 14 pgs.
"Australian Application Serial No. 2013379686, Examination Report dated Jul. 25, 2017", 3 pgs.
"Australian Application Serial No. 2013379686, Response filed Jan. 30, 2018 to Examination Report dated Jul. 25, 2017", 11 pgs.
"Australian Application Serial No. 2013379687, Examination Report dated Aug. 3, 2017", 3 pgs.
"Chinese Application Serial No. 201380051427.8, Office Action dated May 31, 2017", W/English Translation, 12 pgs.
"Chinese Application Serial No. 201380051427.8, Office Action dated Sep. 29, 2016", W/English Translation, 13 pgs.
"Chinese Application Serial No. 201710259694.4, Office Action dated Apr. 18, 2019", w/English Translation, 16 pgs.
"European Application Serial No. 13824063.5, Communication Pursuant to Article 94(3) EPC dated Apr. 29, 2016", 4 pgs.
"European Application Serial No. 13824063.5, Intention to Grant dated Nov. 15, 2016", 41 pgs.
"European Application Serial No. 13824063.5, Response filed Feb. 22, 2016 to Communication Pursuant to Article 94(3) EPC dated Nov. 10, 2015", 53 pgs.
"European Application Serial No. 13824063.5, Response filed Jul. 15, 2016 to Communication Pursuant to Article 94(3) EPC dated Apr. 29, 2016", 6 pgs.
"European Application Serial No. 13824264.9, Communication Pursuant to Article 94(3) EPC dated Apr. 7, 2016", 7 pgs.
"European Application Serial No. 13824264.9, Communication Pursuant to Article 94(3) EPC dated Aug. 8, 2017", 4 pgs.
"European Application Serial No. 13824264.9, Communication Pursuant to Article 94(3) EPC dated Nov. 14, 2016", 4 pgs.
"European Application Serial No. 13824264.9, Intention to Grant dated Feb. 26, 2018", 41 pgs.
"European Application Serial No. 13824264.9, Intention to Grant dated May 22, 2018", 39 pgs.
"European Application Serial No. 13824264.9, Response filed Feb. 19, 2017 to Communication Pursuant to Article 94(3) EPC dated Nov. 14, 2016", 7 pgs.
"European Application Serial No. 13824264.9, Response filed Apr. 28, 2018 to Intention to Grant dated Feb. 26, 2018", 9 pgs.
"European Application Serial No. 13824264.9, Response filed Aug. 2, 2016 to Communication Pursuant to Article 94(3) EPC dated Apr. 7, 2016", 34 pgs.
"European Application Serial No. 13824264.9, Response filed Oct. 27, 2017 to Communication Pursuant to Article 94(3) EPC dated Aug. 8, 2017", 31 pgs.
"European Application Serial No. 18165801.4, Communication Pursuant to Article 94(3) EPC dated Jul. 4, 2019", 5 pgs.
"European Application Serial No. 18165801.4, Extended European Search Report dated Aug. 14, 2018", 10 pgs.
"European Application Serial No. 18165801.4, Response filed Mar. 8, 2019 to Extended European Search Report dated Aug. 14, 2018", 29 pgs.
"European Application Serial No. 18165801.4, Response filed Oct. 15, 2019 to Communication Pursuant to Article 94(3) EPC dated Jul. 4, 2019", w/ English claims, 53 pgs.

(56) References Cited

OTHER PUBLICATIONS

"International Application Serial No. PCT/US2013/065830, International Search Report dated Dec. 12, 2013", 4 pgs.
"International Application Serial No. PCT/US2013/065830, Written Opinion dated Dec. 12, 2013", 6 pgs.
"International Application Serial No. PCT/US2013/077758, International Preliminary Report on Patentability dated Sep. 1, 2015", 8 pgs.
"International Application Serial No. PCT/US2013/077758, International Search Report dated Mar. 25, 2014", 5 pgs.
"International Application Serial No. PCT/US2013/077758, Written Opinion dated Mar. 25, 2014", 7 pgs.
"International Application Serial No. PCT/US2013/077759, International Preliminary Report on Patentability dated Sep. 11, 2015", 12 pgs.
"Japanese Application Serial No. 2015-549868, Amendment filed Jun. 19, 2015", W/ English Translation, 8 pgs.
"Japanese Application Serial No. 2015-549868, Amendment filed Jul. 29, 2016", 8 pgs.
"Japanese Application Serial No. 2015-549868, Notice of Reasons for Refusal dated May 31, 2016", W/ English Translation, 10 pgs.
"Japanese Application Serial No. 2015-559235, Amendment filed Nov. 1, 2016", with English translation of claims, 6 pgs.
"Japanese Application Serial No. 2016-149527, Amendment filed Jan. 31, 2018", w/ English Translation, 8 pgs.
"Japanese Application Serial No. 2016-149527, Amendment filed Dec. 20, 2016", w/ English Translation, 9 pgs.
"Japanese Application Serial No. 2016-149527, Appeal Brief filed Jun. 27, 2018", 14 pgs.
"Japanese Application Serial No. 2016-149527, Decision of Rejection dated Mar. 20, 2018", w/ English Translation, 10 pgs.
"Japanese Application Serial No. 2016-149527, Office Action dated Dec. 12, 2017", w/ English Translation, 8 pgs.
Edwards, Kevin, et al., "Replacable Debrider Blade Module With Latching Mechanism", Potentially Related U.S. Appl No. 13/826,892, filed Mar. 14, 2013, 41 pgs.
Liu, Yimin, et al., "Method and Apparatus for Route Completion Likelihood Display", Potentially related U.S. Appl. No. 13/769,416; mailed on Mar. 12, 2013, 21 pgs.

\* cited by examiner

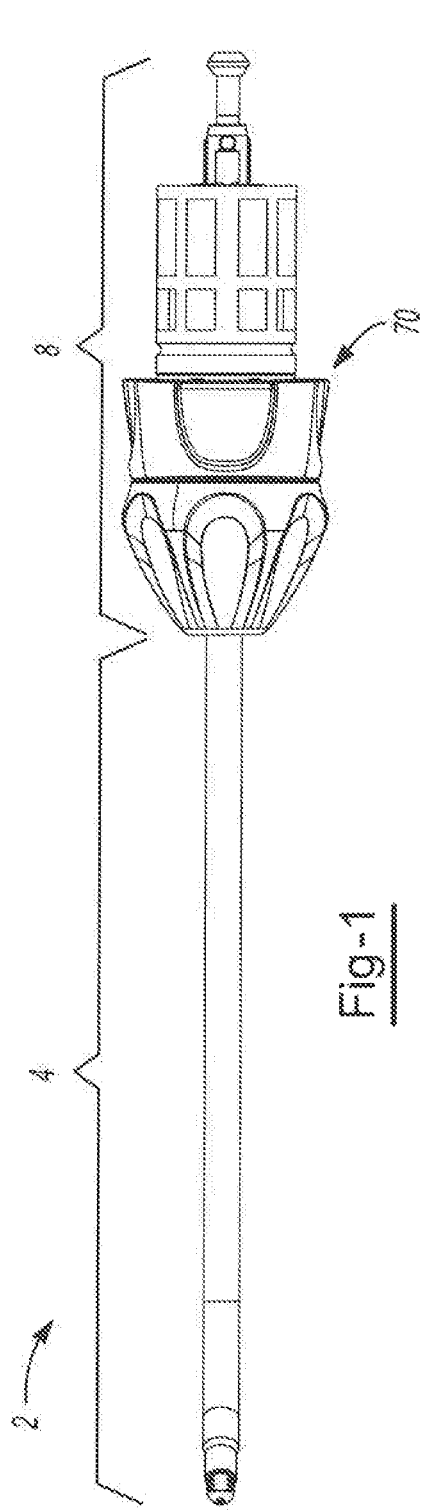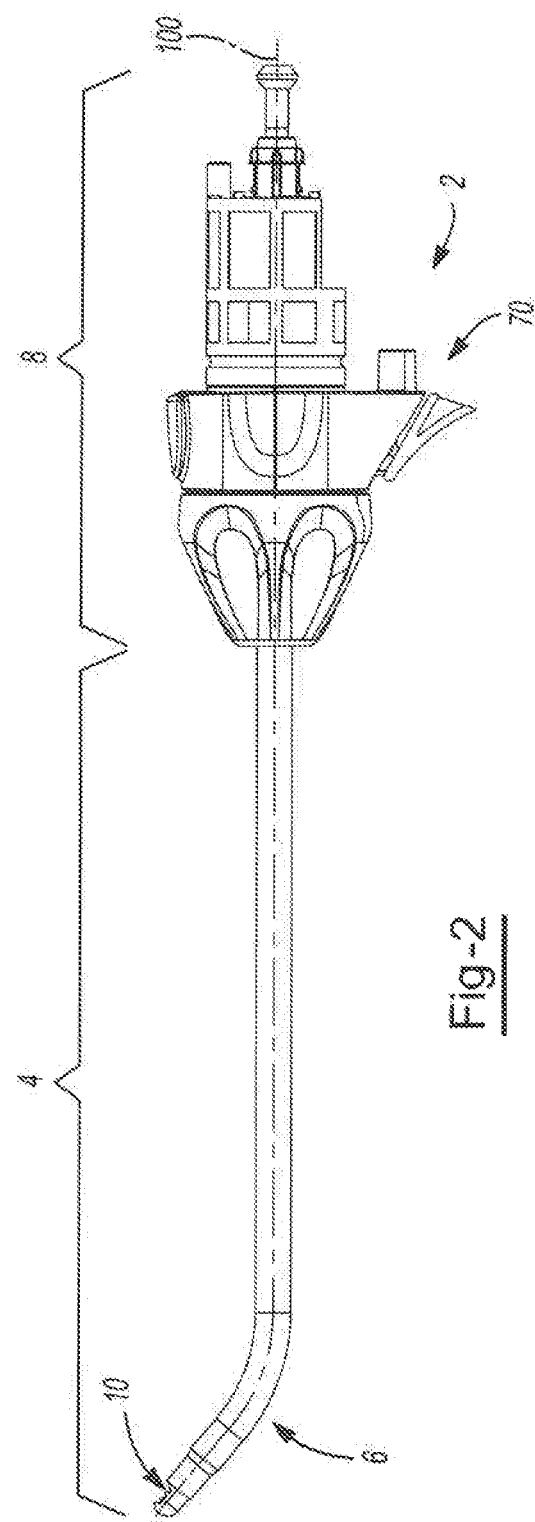

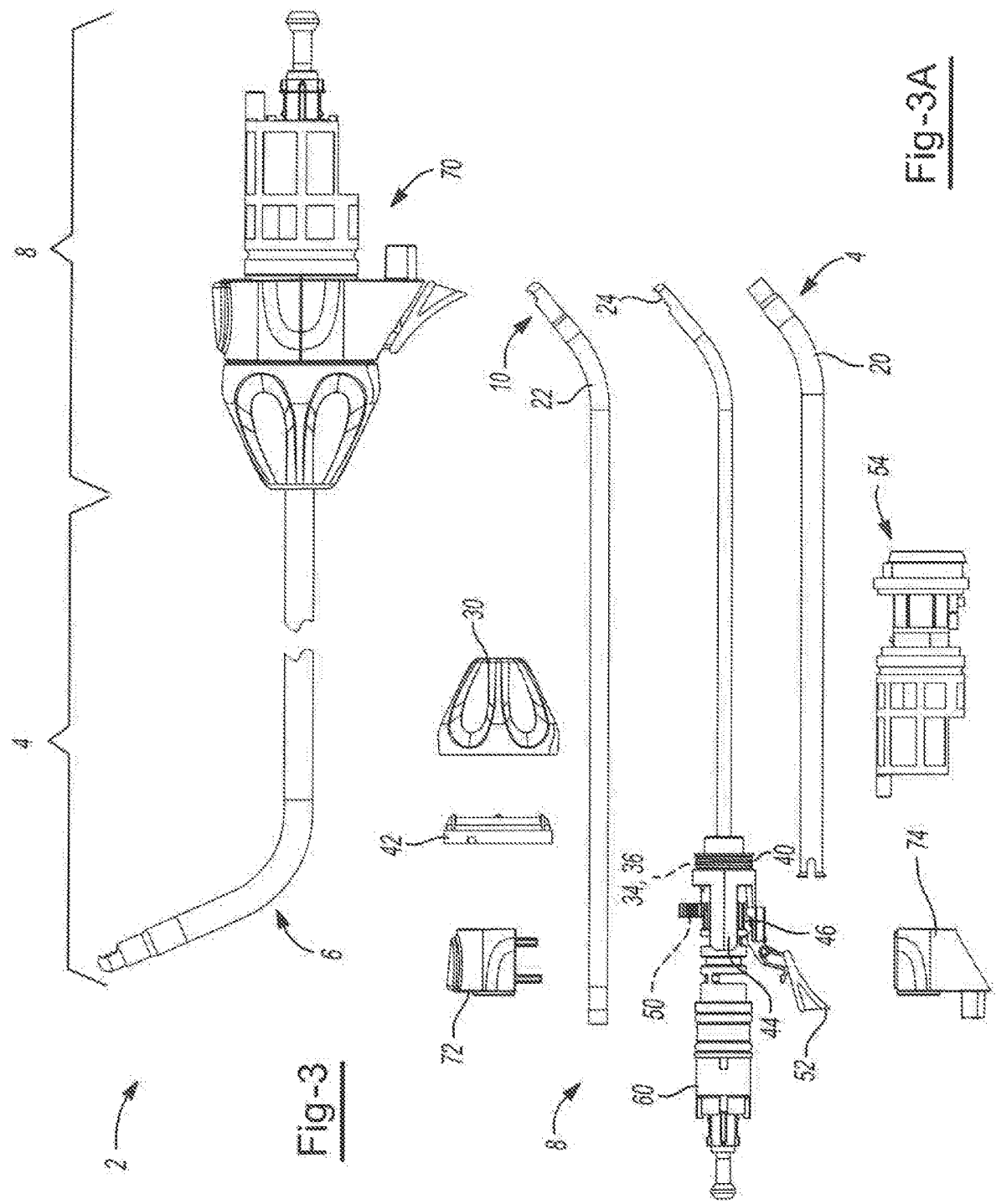

REPLACABLE DEBRIDER BLADE MODULE WITH LATCHING MECHANISM

FIELD

The present teachings generally relate to a debrider blade module, and more specifically a debrider blade module with locking part so that rotation of blades of the blade module can be restricted and/or prevented.

BACKGROUND

Generally, debriders include a handpiece and a cutting portion. The handpiece includes a motor that rotates one or more rotating portions in the cutting portion. The cutting portion includes a cutting window where the cutting window exposes a cutting blade and/or the cutting portion is angled. During use the cutting window and/or the angle of the cutting portion can be oriented by rotating the entire handle. In some instances, the entire cutting portion may be removed from the handpiece rotated and put back in the handpiece so that the cutting window and/or the angled portion is oriented as desired.

Additionally, some handpieces include a rotary knob that may be used to rotate the cutting portion from the handpiece. During use the handpiece may increase in temperature and one or more of the components of the handpiece may thermally expand. The expansion rates of the various components may inhibit movement of the rotary knob so that the rotary knob is difficult to use and/or has limited function. After use, the handpiece and the rotary knob may be placed in an autoclave so that the handpiece is sterilized and subsequently placed in a fluid for rapid cooling. However, the repeated heating and cooling of the handpiece and rotary knob may degrade the rotary knob so that the connection between and the cutting portion and the rotary knob slips and/or sticks so that rotation of the cutting portion is inhibited. In another example, repeated cleaning and/or poor cleaning techniques of the device may result in a buildup of material in the device so that the built-up material inhibits proper function of the rotary knob.

Examples of some surgical instruments may be found in U.S. Pat. Nos. 5,112,299; 5,376,078; 5,492,527; 5,540,708; 5,609,573; 5,620,447; 5,873,886; 6,494,892; 7,247,161; 8,109,956; 8,202,288; U.S. Patent Application Publication No. 2002/0038129; 2004/0243163; 2005/0277970; 2010/0298763; and 2012/0221035 all of which are incorporated by reference herein for all purposes. It would be attractive to have a rotation device that is connected to the cutting portion. It would be attractive to have a locking portion that locks the rotating portion so that when the cutting portion is in use the cutting portion does not rotate. It would be attractive to have a nosecone that rotates an outer tube, an intermediate tube, or both of the cutting portion so that the cutting window and/or the angle portion is rotated.

SUMMARY

The present teachings meet one or more of the present needs by providing: a blade assembly comprising: (a) a tip including two or more tubes, wherein the two or more tubes include at least: (i) an outer tube and (ii) an inner tube; and (b) a mechanical enclosure including: (i) a locking spline having a longitudinal axis; and (ii) a slide lock; wherein the slide lock slides along the longitudinal axis of the locking spline and over the locking spline forming a locked state so that rotational movement of the locking spline, around the longitudinal axis of the locking spline, is prevented: and wherein the outer tube is coupled to the locking spline so that rotational movement of the outer tube, around the longitudinal axis of the locking spline, is prevented during the locked state.

Another possible embodiment of the present teachings comprises: a blade assembly comprising: (a) a tip including three or more tubes, wherein the three or more tubes include at least: (i) an outer tube; (ii) an inner tube; and (iii) an intermediate tube located at least partially between the inner tube and the outer tube; and (b) a mechanical enclosure including: (i) a nosecone having a nosepiece gear; and (ii) a collet having one or more pinion gears that are in communication with the nosepiece gear, wherein the intermediate tube is connected to an outer hub that extends though the collet, the outer hub including a toothed portion that is in communication with the one or more pinion gears so that rotation of the nosecone causes rotation of the intermediate tube.

Another possible embodiment of the present teachings comprises: a blade assembly comprising: (a) a tip including two or more tubes, wherein the two or more tubes include at least: (i) an outer tube; (ii) an inner tube; and (b) a mechanical enclosure including: nosecone having a rotational axis; wherein the outer tube is connected to the nosecone so that rotation of the nosecone causes rotation of the outer tube.

The teachings herein provide rotation device that is connected to the cutting portion. The teachings herein provide a locking portion that locks the rotating portion so that when the cutting portion is in use the cutting portion does not rotate. The teachings herein provide a nosecone that rotates an outer tube, an intermediate tube, or both of the cutting portion so that the cutting window and/or the angle portion is rotated.

BRIEF DESCRIPTION OF THE DRAWINGS

FIG. 1 illustrates a view of a blade assembly with a straight tip;

FIG. 2 illustrates a view of a blade assembly with an angled tip;

FIG. 3 illustrates an angled tip;

FIG. 3A illustrates an exploded view of one embodiment of the angled tip of FIG. 3 with the blade tip in a locked position

DETAILED DESCRIPTION

Figure 2A:
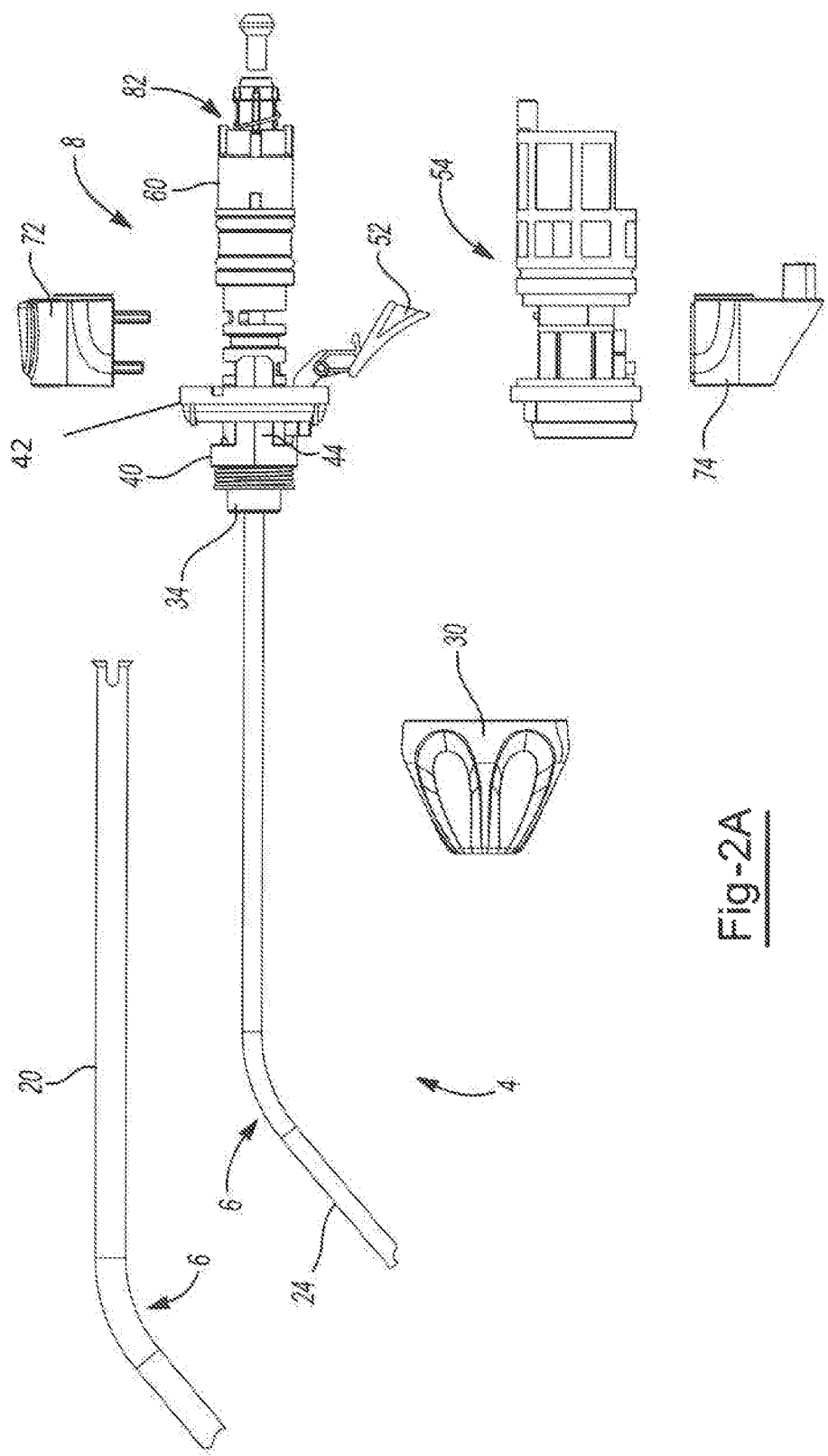
FIG. 2A illustrates an exploded view of one embodiment of the angled tip of FIG. 2 with the blade tip in a locked position

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein provide a debrider and preferably a microdebrider. The debrider generally includes a handpiece and a separable blade assembly. The handpiece includes an aperture that receives a portion of the blade assembly so that the handpiece may drive the blade assembly during use. The handpiece may include a motor and one or more gears that drive one or more rotary cutting tubes of the blade assembly. Other teachings of the handpiece may be gleaned from the teachings herein including those of paragraph Nos. 6-8, 26-45, 061-062, 065, and 70-72 and FIGS. 1-3 of U.S. Patent Application Ser. No. 61/731,919 filed on Nov. 30, 2012 teaching a handpiece and one or more connection portions for driving the separable blade assembly. The blade assembly when installed in the handpiece may form a fixed connection so that the blade assembly does not rotate independently of the handpiece. The handpiece and blade assembly may be separable so that the handpiece, the blade assembly, or both may be cleaned, disposed, or both after use.

Preferably, the blade assembly may be disposable. The blade assembly includes a tip and a mechanical enclosure. The tip may include one or more tubes and preferably two or more tubes. The one or more tubes may be made of any biocompatible material. The one or more tubes may be made of a material that may be used to perform surgery. The one or more tubes may be made of any material that is sufficiently rigid to perform surgery: to be push, pulled, angled, or a combination thereof without bending, breaking; or both. The one or more tubes may be made of a polymer, metal, a natural material, a synthetic material, or a combination thereof. Preferably, the one or more tips are made of stainless steel or a surgical steel. The tip may include at least an outer tube and an inner tube. The tip may include an outer tube, an intermediate tube at least partially disposed within the outer tube, and an inner tube at least partially disposed within the intermediate tube and the outer tube. Each of the two or more tubes may be connected. Preferably, each of the two or more tubes is axially independent of each other so that one or more of the tubes may rotate without rotating the other tubes. For example, an inner tube, an intermediate tube, or both may rotate inside of the outer tube. The one or more tubes may be straight, angled, bent, curved, flex-jointed (e.g., if the outer tube is bent then inner tube may be flexible to rotate within the outer tube), or a combination thereof. The one or more tubes may form one or more angles and the one or more angles may be any angle or combination of angles, include an angled portion, or both. The angled portion may be a rigid bend, an arcuate bend, a sweeping curve, or a combination thereof. The one or more tubes may have an angled portion that forms an angle of about 0 degrees or more, about 15 degrees or more, about 30 degrees or more, about 45 degrees or more, about 60 degrees or more, or about 90 degrees or more. The one or more tubes may have an angled portion that forms an angle of about 150 degrees or less, about 135 degrees or less, about 125 degrees or less, or about 105 degrees or less. Thus, for example in a multiple tube design the outer tube and the inner tube may both be straight and/or angled.

The outer tube may be a sheath that houses all or a portion of an inner tube, an intermediate tube, or both. The outer tube may be any tube that forms an outer surface of the tip so that a fluid, surgical debris, irrigation fluids, or a combination thereof may pass through the outer tube to and/or from a site of interest. The outer tube may be any shape, size, configuration, or a combination thereof so that the outer tube assists in protecting the inner tube, the intermediate tube, or both. The outer tube may be of any size and shape so that the outer tube may be useful for surgery and preferably for minimally invasive surgery. The outer tube may be sufficiently sized so that that one or more tubes may fit within the outer tube and so that a fluid, surgical debris, irrigation fluids, or a combination thereof may pass through the outer tube to and/or from a site of interest. The outer tube includes an inner diameter and an outer diameter. The inner diameter may be sufficiently sized so that one or more and preferably two or more tubes may fit within the inner diameter of the outer tube and fluid, surgical debris, irrigation fluids, or a combination thereof may pass through the outer tube to and/or from a site of interest. The inner diameter may be about 1 mm or more, about 2 mm or more, or about 3 mm or more. The inner diameter may be about 7 mm or less, about 6 mm or less, or about 5 mm or less. The outer diameter may be about ±0.0.1 mm about ±0.5 mm, or about ±1.0 mm of the inner diameter. The diameter of the outer tube may be sufficiently sized so that the outer tube may include an angled portion.

The outer tube may determine the angle of the angled portion of the inner tube, the intermediate tube, or both as discussed herein for the angle of the tip. The outer tube may be rotatable around its own rotational axis, a longitudinal axis of a locking spline, or a combination thereof. The outer tube may be rotatable and/or revolved around a portion of its own longitudinal axis. For example, the outer tube may be bent and a longitudinal axis of the outer tube may follow the bend of the outer tube, and the outer tube may rotate around the linear portion of the longitudinal axis so that the bend in outer tube may be rotated from a first position to a second position. The outer tube may be rotatable around a longitudinal axis of the mechanical enclosure, an axis parallel to the longitudinal axis of the mechanical enclosure, or a combination thereof. The outer tube may include one or more slots.

The one or more slots may be located at any location along the outer tube so that the outer tube forms a fixed connection with the nosecone, the locking spline, or both. Preferably, the outer tube includes one or more slots at a proximal end (i.e., an and proximate to the user, within the mechanical enclosure, or both). The slots may be an absence of material, a cut, a slit, a bend, a taper, a flared portion, or a combination thereof. Preferably, the outer tube includes two slots on an end that is adjacent to the nosecone so that the outer tube may be fixedly secured to the nosecone, the outer tube may be fixedly connected to a locking spline, or both. The one or more slots of the outer tube may be connected to the locking spline so that a cutting window in the outer tube, a cutting window in the intermediate tube, or both may be rotated around the longitudinal axis of the outer tube, the longitudinal axis of the intermediate tube, or both as discussed herein.

The outer tube may include a cutting window. The cutting window may be a window that exposes all or a portion of a distal end of the inner tube, all or a portion of a distal end of the intermediate tube, or both so that during use the inner tube rotates and forms a cutting surface for performing a surgery. The outer tube may be free of a cutting window. The outer tube may include an open end so that all or a portion of the inner tube, an intermediate tube, or both extends out of the open end. The open end, the cutting window, or both may include a taper that reduces the diameter of the outer tube. The open end, the cutting window, or both may form a snug connection, a journalled connection, an interference fit, a friction fit, or a combination thereof with the intermediate tube, the inner tube or both, so that the inner tube, the intermediate tube, or both are prevented from moving axially towards the distal end of the tip, moving laterally, or both, but the inner tube, the intermediate tube, or both may rotate around a longitudinal axis of the outer tube.

The intermediate tube may extend through all or a portion of the outer tube. The intermediate tube may extend all of the way through one or both ends of the outer tube. The intermediate tube may include a window for exposing all or a portion of an inner tube. The intermediate tube may include an open end so that the inner tube may extend out of the intermediate tube. The window of the intermediate tube, the outer tube, or both may be sufficiently large so that a sufficient amount of the inner tube may be exposed for debriding (e.g., cutting, shaving, smoothing, removing, the like, or a combination thereof). The window of the intermediate tube, the outer tube, or both may be sufficiently small so that the device may be used for minimally invasive debriding. The window of the outer tube, the intermediate tube, or both may be substantially the same size. The window of the intermediate tube, the outer tube, or both may be located in a distal end region of the tip (e.g., a region of the tip proximal to a patient and distal from the user). The window of the intermediate tube, the outer tube, or both may extend around about 15 degrees or more, about 30 degrees or more, about 45 degrees or more, about 60 degrees or more, about 90 degrees or more, about 115 degrees or more, about 135 degrees or more, or about 150 degrees or more. The window of the intermediate tube, the outer tube or both may extend around about 300 degrees or less, about 270 degrees or less, about 235 degrees or less, or about 200 degrees or less. The inner tube may have a cutting surface that is substantially the same size as the window so that the cutting window and the cutting surface of the cutting window form two opposing cutting portions that assist in debriding.

The inner tube may extend through all or a portion of the intermediate tube, the outer tube, or both. The inner tube may be free to rotate independently of the outer tube, the intermediate tube, or both. The inner tube may extend through one or both ends of the outer tube, the intermediate tube, or both. The inner tube may have a grinding tip that extends all of the way through the outer tube, the intermediate tube, or both so that the grinding tip is exposed at 360 degrees. The inner tube may connect with a coupling device that transfers power from the motor in the handpiece to the inner tube so that the inner tube rotates around an axis. The inner tube may be connected to and/or include a inner hub.

The inner hub may be any device that may assist in coupling the inner tube to the motor, in rotating the inner tube, in forming a fixed connection on the inner tube so that the inner tube is not displaced along the longitudinal axis, or a combination thereof. The inner hub may include one or more teeth for forming a rotatable connection with an adjacent component. One or more bias members may extend over all or a portion of the inner hub to assist is forming a connection, removing a connection, ensuring that the connection remains secure, or a combination thereof. The bias member may be any bias member discussed herein. Preferably, the bias member is a spring. The bias member may be located proximate to one or more seals. The one or more seals may be any seal that prevents fluid leakage. The one or more seals may be located at an end of the inner hub, at an end of the inner tube, the intermediate tube, the outer tube, or a combination thereof so that a fluid, surgical debris, irrigation fluids, or a combination thereof is prevented from leaking into the handpiece and is urged to extend through the tubes in the handpiece. The inner tube, the inner hub, or both may extend through a encapsulation connector. The encapsulation connector may assist in preventing lateral movement of the inner tube, the intermediate tube, the outer tube, or a combination thereof. Preferably, the inner tube extends through the encapsulation connector so that the encapsulation connector prevents lateral movement of the inner tube and monitors rotation of the Inner tube. The encapsulation connector may include two or more transmitters that are in magnetic communication with the inner tube, the inner hub, the outer hub, or a combination thereof. Preferably, the two or more transmitters of the encapsulation connector magnetically monitor the position of the outer hub and/or the window in the outer tube, the intermediate tube, or both with respect to the position of the window. Other teachings regarding the encapsulation connector, the two or more transmitters, the magnetic communication, or a combination thereof may be gleaned from the teachings herein, including those Paragraph Nos. 008-0014 and 0035-0055; and FIGS. 2-14 of U.S. patent application Ser. No. 13/251,493, filed on Oct. 3, 2011, incorporated by reference herein for all purposes regarding the encapsulation connector, the two or more transmitters, or the magnetic communication. The encapsulation connector and the outer hub may be located adjacent to each other, may cover all or a portion of the adjacent part, may form a sealed connection or a combination thereof. Alternatively, other teachings regarding rotating one or more of the tubes relative to each other may be gleaned from the teachings herein, including those of Paragraph Nos. 004-005, 0012-0038 and FIGS. 1A-4C of U.S. patent application Ser. No. 13/796,412, filed on Mar. 12, 2013, incorporated by reference herein for all purposes regarding a lock selector, bias device, and an actuation selector.

The outer hub may fully and/or partially extend into a handpiece and assist in creating a fixed connection between the disposable blade and a handpiece. The outer hub may be entirely located outside of the handpiece. The outer hub may be any device that is fixedly connected to the outer tube, the intermediate tube, or both. The outer hub may be fixedly connected to the outer tube, the intermediate tube, or both so that axial movement, relative to the axis of the outer hub, of the outer tube, the intermediate tube, or both is substantially prevented, eliminated, or both. The outer hub may be any device that facilitates rotational movement of one or more of the tubes during rotation of one or more parts that are adjacent to the one or more tubes, connected to the one or more tubes, or both. The outer hub may be fixedly connected to an outer tube, a nosecone, or both so that upon rotation of the nosecone the outer tube is rotated by its connection with the outer hub. The outer hub may be fixedly connected to the outer tube, the intermediate tube, or both so that when the outer hub rotates the outer tube, the intermediate tube, or both rotate. The outer hub may be fixedly connected to the intermediate tube, the outer tube, or both so that when the nosecone is rotated the intermediate tube, the outer tube, or both are rotated. The outer hub may extend into, extend around, extend into contact with, or a combination thereof one or more adjacent parts so that upon movement of the one or more adjacent parts the outer hub is rotated along with the outer tube, the intermediate tube, or both. The outer hub may be rotated by a portion having an interfitting torque transmitting piece.

The interfitted torque transmitting piece may be any device that transfers a force, torque, or both from one component to another component. The interfitting torque transmitting piece may include ribs, teeth, a helically wrapped track, or a combination thereof. The interfitted torque transmitting piece may be smooth, free of teeth, free of ribs, or a combination thereof. The interfitted torque transmitting piece may be contacted and rotated by a belt, a pulley, a flat pliable material, or a combination thereof. Preferably, the interfitted torque transmitting piece is a gear portion, a cog portion, a worm gear portion, an inner hub portion, or a combination thereof of the outer hub. Preferably, the interfitted torque transmitting piece of the outer hub may be a toothed portion.

The toothed portion may be any portion of the outer hub that is located juxtaposed to one or more adjacent components that may contact the toothed portion so that upon rotation of the one or more adjacent components the toothed portion may rotate the outer hub. Preferably, a forward portion (e.g., distal portion that is axially located distal from the handpiece) of the outer hub includes a toothed portion having a plurality of teeth. The toothed portion may extend around all or a portion of a circumference of the outer hub so that the outer hub may be used to rotate an intermediate tube, an outer tube, or both. Preferably, the toothed portion may extend 360 degrees around the outer hub so that the outer tube, the intermediate tube, or both may be fully rotated in a clockwise direction, a counterclockwise direction, or both. The toothed portion may be contacted by one or a plurality of pinion gears.

The one or more pinion gears may be any device that may contact the interfitted torque transmitting piece, the toothed portion, or both of the outer hub. The one or more pinion gears may be any gear that rotates around an axis and transfers torque, force, movement, or a combination thereof from and/or to one or more adjacent surfaces, components, pieces, or a combination thereof. The one or more pinion gears may form a substantially a mirror image to the interfitted torque transmitting piece, the toothed portion, or both so that one or more pinion gears and the interfitted torque transmitting piece, the toothed portion, or both form a rotational connection, an interconnection, or both for transferring a force, torque, or both. The one or more pinion gears may be sufficiently large so that the pinion gears rotate the intermediate tube, the outer tube, or both without the user having to reposition his or her hand to complete a desired rotation. The one or more pinion gears may be sufficiently small so that the one or more pinion gears do not prevent one or more components from extending through the through hole in the collet. The one or more pinion gears and the interfitted torque transmitting piece, the toothed portion, or both may have a gearing ratio. For example, one complete rotation of the one or more pinion gears may rotate the outer hub 1 time thus having a gearing ratio of 1:1. The gearing ratio may be any ratio so that upon movement of the one or more pinion gears the outer hub is rotated a sufficient amount so that a window in the outer tube, the intermediate tube, or both rotates about 60 degrees or more, about 90 degrees or more, about 120 degrees or more, or about 180 degrees or more. The gearing ratio of the one or more pinion gears to the interfitted torque transmitting piece, the toothed portion, or both may be about 1:0.5 or more, about 1:0.7 or more, about 1:1 or more, or about 1:1.2 or more. The gearing ratio of the one or more pinion gears to the interfitted torque transmitting piece, the toothed portion, or both may be about 1:5 or less, about 1:4 or less, about 1:3 or less, or about 1:2 or less. The tip may include a sufficient number of pinion gears so that the outer hub is rotated in the same direction as a user rotates. The tip may include an odd number of pinion gears or an even number of pinion gears. Preferably, tip includes an even number of pinion gears. More preferably, the tip includes at least two pinion gears so that the outer hub is rotated in the same direction as a user rotates a movable portion connected to the at least two pinion gears. The one or more pinion gears may be connected to a collet.

The collet may extend partially and/or entirely into a handpiece and assist in creating a connection between the disposable blade and the handpiece. The collet may form a fixed connection with the handpiece so that the collet, the disposable blade, or both are free of rotational movement, lateral movement, longitudinal movement, or a combination thereof. The collet may be any device that is stationary within the mechanical enclosure. A blade module may be connected to the collet, around the collet, or both so that the blade module forms a stationary connection relative to the handpiece, the collet, or both. The collet may be a stationary gripping portion for a user. The collet may form a frame for the tip, the mechanical enclosure, or a combination thereof. The collet may be any device that includes one or more through holes for one or more components to extend through. For example, one or more tubes, a slide lock, a lock lever, an outer hub, or a combination thereof may extend through the collet. Preferably, at least the outer hub extends at least partially through the through hole in the collet. For example, the outer hub may include one or more seals around an outer periphery that contact an inner surface of the collet so that the seals form a sealed connection therebetween. The collet includes a longitudinal axis. The longitudinal axis may extend through a center of the collet, through a center of the through hole in the collet, or both. The through hole may extend through a center of the collet, may be offset from center, or both. For example, the locking spline, the slide lock, the one or more tubes, or a combination thereof may be offset from an axis extending though the center of the collet. Preferably, however, the collet, the locking spline, the slide lock, and the one or more tubes are all concentric, aligned along the longitudinal axis of the collet, or both. The outer hub and the collet may form a sealed connection. The sealed connection between the collet and the outer hub may allow for rotational movement of the outer hub relative to the collet and maintain the sealed connection. Preferably, during use a user grips the collet or a piece fixedly and/or rotatably connected to the collet so that the user may rotate one or more adjacent parts, manipulate the disposable blade, perform a procedure, or a combination thereof. The collet may include one or more connection surfaces so that one or more adjacent parts discussed herein may be connected to the collet. The collet may include one or more support pins for supporting the one or more pinion gears.

The one or more support pins may be any device that provides rotational support for the pinion gears. The one or more support pins may be one or more axes, bearing surfaces, supports, or a combination thereof. The one or more support pins may be any device that supports the one or more pinion gears in a low friction rotational movement. Preferably, the one or more pinion gears may be connected to the collet via the one or more support pins. More preferably, the one or more pinion gears may be rotationally movable relative to the collet but axially fixed to the collet. For example, the one or more pinion gears may be fixed to the support pins so that they cannot slide along their rotational axis; however, the pinion gears are free to rotate around the rotational axis. The one or more pinion gears, the one or more support pins, or both may be located at any position on the collet. Preferably, the one or more support pins, the one or more pinion gears, or both are located at a distal end of the collet (i.e., the end of the collet closest to the nosecone and farthest from the user). More preferably, the one or more support pins, the one or more pinion gears, or both may be located substantially out of the through hole opening so that one or more components may pass through the through hole. Even more preferably, the one or more support pins, the one or more pinion gears, or both are located on the collet so that the one or more pinion gears connect to the interfitted torque transmitting piece, the toothed portion, or both of the outer hub located proximate to and/or extending through the through hole opening. The one or more pinion gears may form a connection, an interfitted connection, a torque transfer connection, or a combination thereof with one or more nosepiece gears.

The one or more nosepiece gears may be any gear that transfers a rotational force from a user to one or more of the tubes discussed herein. The one or more nosepiece gears may be any shape, size, or configuration so that upon movement of the nosecone, one or more the nosepiece gears move one or more adjacent disposable blade components. The nosepiece gear may be circular, oval, one or more adjoining segments, one continuous piece, or a combination thereof. The one or more nosepiece gears may be an atlas gear, a planetary gear, a gear that may extend around an inside periphery of an adjacent component, the nosecone, or both. The one or more nosepiece gears may be fixedly connected, permanently connected, an integral part of, or a combination thereof a nosecone of the disposable blade. The one or more nosepiece gears may form a connection with the nosepiece so that when a user rotates the nosepiece, the one or more nosepiece gears are rotated. For example, the nosepiece gear and the nosecone may be two discrete pieces that are connected. In another example, the nosepiece gear may be integrally formed in an interior of the nosepiece so that they are one part. The one or more nosepiece gears may include one or more bumps, one or more projections, or both that prevent rotation of the nosepiece gear independent of the nosecone. The one or more nosepiece gears may extend partially and/or fully around an inside, an outside, or both of the nosepiece. Preferably, the one or more nosepiece gears extend 360 degrees around an inside of the nosepiece and form an interfitted connection with the one or more pinion gears. The one or more nosepiece gears may be any device that may transfer torque, a rotational force, or both to the one or more tubes, the outer hub, the pinion gears or a combination thereof either directly or indirectly. In one preferred example, the nosepiece gear may connect with two pinion gears that are connected to a toothed portion of the outer hub, which is connected to an intermediate tube, an outer tube, or both so that upon rotation of the nosecone the rotational force is transferred to the intermediate tube, the outer tube, or both so that a window in the intermediate tube, the outer tube, or both is oriented as desired. The one or more nosepiece gears may be a belt that may transfer torque, a rotational force, or both directly from the nosecone to the outer tube, the intermediate tube, or both. Preferably, the one or more nosepiece gears include one or more teeth that form an interfitted connection with one or more adjacent toothed gears. The one or more nosepiece gears and the one or more pinion gears may have a gear ratio. The gear ratio may be any ratio so that upon movement of the nosecone, the one or more nosepiece gears or both the outer tube, the intermediate tube or both rotate about 60 degrees or more, preferably about 90 degrees or more, and more preferably about 120 degrees or more. The gear ratio of the nosepiece gear to the pinion gears may be about 1:1 or more, preferably about 1:1.5 or more, more preferably about 1:2 or more, and more preferably about 1:2.5 or more. The gear ratio of the nosepiece gear to the pinion gears may be about 1:10 or less, about 1:5 or less, or about 1:3 or less. In one preferred example, each rotation of the nosepiece gear rotates the pinion gears about 2.5 times and the outer hub about 2 times. Preferably, a nosecone includes only one nosepiece gear.

The nosecone may be any part of the disposable blade that rotates the orientation of the one or more tubes, rotates the one or more windows of the one or more tubes, or both. The nosecone may be any portion that may be gripped by a user. The nosecone may be a distal most part of the mechanical enclosure, may be the part of the mechanical enclosure that is located closest to the patient, a piece that one or more and preferably all of the tubes extend through, or a combination thereof. The nosecone includes a rotational axis. The nosecone and the nosepiece gear may have rotational ratio. The rotational ratio of the nosecone to the nosepiece gear may be about 1:0.5 or more, preferably about 1:0.8 or more, and more preferably about 1:1 or more. The rotational ratio of the nosecone to the nosepiece gear may be about 1:2 or less, about 1:1.5 or less, or about 1:1.2 or less. Preferably, the rotational ratio of the nosecone to the nosepiece gear is about 1:1. The nosecone may prevent the one or more tubes from laterally moving during use. For example, the nosecone may provide stability around the periphery of the one or more tubes so that the one or more tubes are substantially fixed in a direction transverse to the rotational axis of the one or more tubes. The nosecone may form a fixed connection directly and/or indirectly with one or more of the tubes. The nosecone may form a fixed connection with the outer tube, the intermediate tube, or both so that rotation of the nosecone rotates the outer tube, the intermediate tube, or both. Preferably, in a three tube system the outer tube is fixedly and/or rotatably connected directly and/or indirectly to the nosecone. The nosecone may include one or more complementary pieces that form an interlock with a feature in the outer tube, the intermediate tube, or both. The nosecone may include a tab that forms a fitted connection with a slot in the outer tube, the intermediate tube, or both. Preferably, the nosecone includes one or more locking splines.

The one or more locking splines may be any device that extends into the nosecone and forms a lockable connection with one or more adjacent parts of the disposable blade. The one or more locking splines may be directly and/or indirectly connected to the nosecone. The one or more locking splines may be free of a fixed connection with the nosecone. For example, the nosecone may be rotatable independently of the locking spline or vice versa. The one or more locking splines may be integrally formed with the nosecone, may be fixedly connected to the nosecone, may be removably connected to the nosecone, or a combination thereof. The one or more locking splines may include a longitudinal axis and may extend from the nosecone along the longitudinal axis. The one or more locking splines may include a through hole that extends along the longitudinal axis and the one or more tubes may extend through the through hole. The through hole may be planar, may be tapered, may include a tapered portion, or a combination thereof so that axial movement of the outer tube, the intermediate tube, or both through the nosecone, the locking spline, or both is minimized and/or substantially prevented. The through hole may be connected to a portion of the outer tube, the intermediate tube, or both by a press fit connection, an interference fit, a fastener, gluing, a taper, mechanical slot/spline, slip fit, or a combination thereof. Preferably, in a two tube system the nosecone is fixedly connected to the locking spline, the outer tube, the outer hub, or a combination thereof so that the nosecone, the locking spline, the outer tube, the outer hub, or a combination thereof cannot be moved independently of one another. More preferably, in a two tube system the outer tube is connected to the outer hub, and the locking spline and outer hub are connected to the nosecone so that when the slide lock is engaged to the locking spline, the outer hub, and the outer tube are prevented from rotation. The one or more locking splines may include one or more tabs adjacent to the through hole.

The one or more tabs may be any feature that is complementary to one or more slots in the outer tube, the intermediate tube, or both. The one or more tabs may be any feature that assists in forming a fixed connection, prevents independent rotational movement, or both of the outer tube, the intermediate tube, or both relative to the nosecone, the locking spline, or both. The one or more tabs may extend into and/or through a portion of the outer tube, the intermediate tube, or both. The one or more tabs may be located at a proximal end of the locking spline (i.e., an end of the locking spline most proximal to a user), partially and/or fully within the through hole, or both. Preferably, in the three tube system the outer tube includes slots and the locking spline includes tabs so that the outer tube forms a fixed connection with the locking spline so that the outer tube and the locking spline cannot be rotated independently, and the nosecone and the locking spline are free of a connection so that the nosecone and locking spline may be independently rotated. The locking spline may include one or more ribs.

The one or more ribs may be any feature that prevents independent rotational movement of a complementary part, the nosecone, or both. The one or more ribs may be sufficiently sized and spaced so that a complementary part forms a fixed connection with the locking spline so that independent rotational movement is prevented. Preferably, the one or more ribs are located on an outer periphery of the locking spline. The one or more ribs may extend in an axial direction relative to the rotational axis of the one or more tubes, parallel to the rotational axis, or both. The one or more ribs may be disposed around a circumference of the locking spline. The one or more ribs may be spaced apart so that a portion of a complementary part may extend between the one or more ribs and form a fixed connection. The one or more ribs may include a tapered portion that assists in creating a fixed connection with a complementary part, assists in aligning the ribs with one or more corresponding ribs and/or teeth on a complementary part, or both. The tapered connection preferably may be located at a proximate portion so that a complementary part may slide over the locking spline to form a connection and the distal portion of the locking spline remains in contact with the nosecone. The complementary part may be any part that may move into contact with and form a fixed connection with the locking spline so that the locking spline is immobilized during the fixed connection. Preferably, the complementary part is a slide lock.

The slide lock may be any part of the disposable blade that may be moved axially along the rotational axis of the one or more tubes, the longitudinal axis of the locking spline, or both so that when engaged with the locking spline rotational movement is prevented and/or substantially eliminated of one or more adjacent parts. The slide lock may include one or more teeth and preferably a plurality of teeth. The one or more teeth may correspond with the one or more ribs in the locking spline so that the teeth and ribs form an alternating configuration. The one or more teeth and the one or more ribs may form a fixed connection that prevents rotational movement, forms a locked state, or both. One or more tubes may extend through a through hole in the slide lock. The slide lock may be any device that may be moved between and form a locked position or locked state, an unlocked position or unlocked state, or both. The slide lock may move within the collet, into and out of the collet, along an axis of the collet, be substantially housed within the collet, or a combination thereof. The slide lock and collet may form a mating relationship so that the collet prevents rotational movement of the slide lock in a locked position, an unlocked position, or both. The slide lock may have one or more rails that slide within one or more corresponding tracks in the collet.

The one or more rails may be any feature of the slide lock that may form a connection with an adjacent piece of the tip so that rotation around the one or more tubes is prevented. The one or more rails may be a piece of the slide lock that extends from the slide lock and forms a ridge, a shoulder, an extended surface, or a combination thereof that contacts an adjacent ridge, shoulder, extended surface, or a combination thereof of an adjacent part so that rotational movement of the two parts relative to each other is substantially limited and/or prevented. Preferably, the one or more rails may have an upper surface and a lower surface that extend between and into a track formed in the collet. The one or more rails may be an extension from the slide lock. The one or more rails may be any size and shape so that the rails form a fixed connection with an adjacent part. The one or more rails may be square, rectangular, round, oval, diamond, symmetrical, asymmetrical, ribbed, planar, non-planar, geometric, non-geometric, or a combination thereof. Preferably, the slide lock includes at least two generally rectangular rails that are substantially parallel so that the rails assist in sliding the slide lock along the axis of the one or more tubes and prevent rotational movement of the slide lock around the axis. The track may be any surface within and/or along the collet that may include an upper surface and a lower surface that forms a ridge, a shoulder, an extended surface, or a combination thereof. The collet may include one or more tracks, preferably two or more tracks, and most preferably three tracks. The one or more tracks may be a recess and/or a through hole in an internal side wall, an external sidewall, or both of the collet. The one or more tracks may be an absence of material in a sidewall of the collet that one or more of the tracks extends into, through, or both. The one or more tracks may be a combination of a through hole, a recess, and a sliding surface that assists in preventing rotational movement of the slide lock relative to the collet. The one or more tracks may be any shape, size, and configuration that substantially mirrors the shape, size, and configuration of the rails so that the rails slide axially along the tracks and the tracks prevent rotational movement around the axis of the one or more tubes. One of the one or more rails may be an actuation connection.

The actuation connection may be any part of the slide lock that forms a connection with a lock lever so that a user can actuate the lock lever to axially move the slide lock. The actuation connection may be fixedly connected, rotatably connected, removably connected, or a combination thereof to the slide lock. The actuation connection may connect with the lock lever so that the lock lever may move the slide lock axially into connection with the locking spline. The actuation connection may include one or more features that may be pushed and/or pulled by the lock lever so that the slide lock is moved. All or a portion of the actuation connection may be flat, angled, tapered, or a combination thereof so that during locking and/or unlocking the lock lever slides within the actuation connection.

The lock lever may be any device that has a portion that is internal of the mechanical enclosure and a portion that is external of the mechanical enclosure so that a user can lock and unlock the position of the outer tube, the intermediate tube, the inner tube, or a combination thereof for rotational movement. The lock lever may include one or more shoulders that connect to the actuation connection, a portion of the blade module, or both. The lock lever may pivot around the one or more shoulders forming a locked position and an unlocked position. The mechanical enclosure may include a seat that holds one or both of the shoulders. The mechanical enclosure may include a blade module and the lock lever may extend through a portion of the blade module so that a portion of the lock lever is exposed for actuation by a user. The blade module may include a control enclosure and a connection enclosure and the lock lever may extend through and/or be connected to one or both of the control enclosure and the connection enclosure. Preferably, the lock lever is in communication with and extends through a portion of the control enclosure. The control enclosure may include one or more through holes so that the lock lever may extend through into and into communication with the slide lock. The lock lever may include a hook that connects the lock lever to the actuation connection. The lock lever may include a locking tab. The locking tab may be any part of the lock lever that holds the lock lever in a locked position or locked state, an unlocked position or unlocked state, or both. Preferably, the locking tab forms a secure connection to the mechanical enclosure so that during use rotation of the outer tube, the intermediate tube, the inner tube, or a combination thereof changing the direction of the angled portion is prevented. For example, when the lock lever is in the locked state the nosecone may rotate the intermediate tube, and the inner tube may rotate so that cutting may be performed, but the rotation of the angled portion of the outer tube, the intermediate tube, and the inner tube around the longitudinal axis may be prevented so that the orientation remains constant. More preferably, the locking tab forms a secure connection to a locking feature on the connection enclosure so that lock lever is secured when the lock lever is in the locked position, the unlocked position, or both. The connection enclosure, the control enclosure, or both of the blade module may be located at any location within the mechanical enclosure. The control enclosure may include one or more electrical parts (i.e., circuitry), one or more mechanical parts, or both. The interchangeable tips may include mechanical functionality including a stylet, one or more connecting tabs, a drive attachment, or a combination thereof so that the mechanical functionality may perform one or more of the procedures discussed herein. The interchangeable tip may include an enclosure that houses the circuitry. Other teachings regarding the blade circuitry, connectors, identification circuits, control circuits, connectors, or a combination thereof may be gleaned from the teachings herein, including those of Paragraph Nos.; 5-9 and 0024-0053 and FIGS. 1-7D and corresponding verbal description in paragraphs 0054-0064 of U.S. patent application Ser. No. 13/803,380, filed on Mar. 14, 2012, incorporated by reference herein for all purposes regarding the blade circuitry, connectors, identification circuits, control circuits, connectors, detection circuits, or a combination thereof, all of which may be incorporated into the mechanical enclosure.

The mechanical enclosure may be any device that houses one or more moving parts of the disposable blade. The blade module may be a fixed portion that the user grips. The blade module may be fixed relative to the nosecone. The mechanical enclosure may include one or more functional buttons. Preferably, the blade module includes at least a control enclosure and a connection enclosure that form a portion of the mechanical enclosure. More preferably, the connection enclosure includes a seat that forms a movable connection, a pivotable connection, or both with the lock lever so that the lock lever may be moved between a locked position and an unlocked position. The lock lever may move axially forward in the distal direction and pivot around the seat of the connection enclosure as the lock lever is moved backwards in the proximal direction. For example, in a locking sequence the lock lever may "teeter totter" (i.e., one end may move in a first direction and the opposing end may move in the opposite direction). The lock lever may be actuated by a bias member when a connection between the locking tab and the locking feature is removed.

The one or more bias members may be located at any location within the mechanical enclosure so that that bias member assists in moving the slide lock, the lock lever, or both from a locked position to an unlock position, or vice versa. The bias member may be any member that assists in moving the slide lock to the unlock position, towards a proximal end of the disposable blade, away from the locking spline, or a combination thereof. The bias member may move the slide lock along the longitudinal axis of the locking spline; the rotational axis of the outer tube, the intermediate tube, the inner tube, or a combination thereof; the longitudinal axis of the collet, the longitudinal axis of the outer hub, or a combination thereof. The bias member may be a spring, a piece of rubber, the like, or a combination thereof that assists in moving the slide lock, the lock lever, or both. Preferably, the bias member extends over the locking spline so that when the slide lock extends over the locking spline the bias member is compressed between the nosecone and the slide lock and presses against the slide lock. The bias member may extend over the locking spline and one or more shims.

The one or more shims may be located between the locking spline and the nosecone and may assist in axially spacing the locking spline from the nosecone, preventing a fixed connection between the locking spline and the nosecone, or both. The one or more shims may only be used in the two tube system or the three tube system.

FIG. 1 illustrates a disposable blade 2 has tip 4 that is angled. The tip 4 is connected to a mechanical enclosure 8. The mechanical enclosure includes a blade module 70 for housing components of the disposable blade 2.

FIG. 2 illustrates a disposable blade 2 has a tip 4 with an angled portion 6 and a window 10. The tip 4 is connected to a mechanical enclosure 8. The mechanical enclosure includes a blade module 70 for housing components of the disposable blade 2. The tip 4 has a rotational axis 100 that conforms to the shape of the angled portion 6 so that the tip 4 along its length rotates around the rotational axis 100.

Figure 2B:
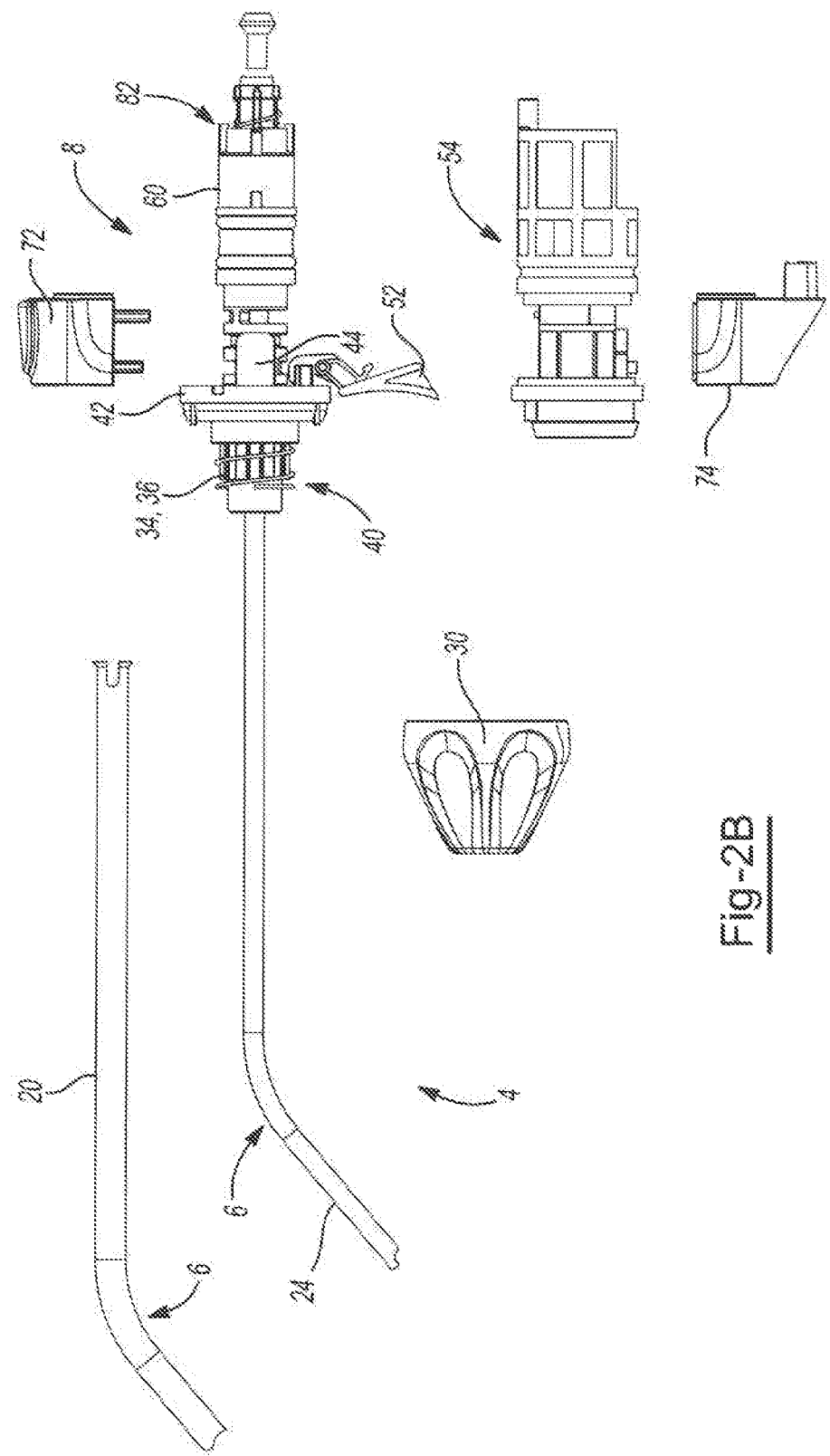
FIG. 2B illustrates an exploded view of one embodiment of the angled tip of FIG. 2 with the blade tip in an unlocked position.

FIGS. 2A and 2B illustrate an exploded view of the disposable blade of FIG. 2 in a locking position. The tip 4 includes an outer tube 20 and an inner tube 24. Both the outer tube 20 and the inner tube 24 include an angled portion 6. The tip 4 connects to the mechanical enclosure 8 by extending through the nosecone 30. The nosecone 30 includes a shim 32 (not shown) for axially spacing the locking spline 34 and biasing member 40 within the nosecone 30. A slide lock 44 is in communication with a lock lever 52. The lock lever 52 is used to move the slide lock 44 between a locking position (as shown in FIG. 2A) and a non-locked position (as shown in FIG. 2B). When the lock lever 52 is moved to the lock position, the lock lever 52 pushes the slide lock 44 over the locking spline 34 so that ribs 36 on the locking spline 34 are engaged with teeth 48 (not shown) on the slide lock 44. An optional nosepiece gear 42 extends into the nosecone 30 and extends around the slide lock 44. The nosecone 30 when rotated rotates a window 10 (not shown) in the tip 4. The collet 54 covers an outer hub 60 that rotates during operation of the disposable blade. A control enclosure 72 and a connection enclosure 74 form an enclosure behind the nosecone 30. At least a portion of the slide lock 44 and assist in supporting the lock lever 52. At least a portion of the outer hub 60 extends beyond the control enclosure 72 and the connection enclosure 74 so that the outer hub 60 assists in forming a connection with a motor (not shown). A ring 82 is located in an end region of the outer hub 60 and assist in sealing the tip. As is illustrated in FIG. 2A the bias member 40 is compressed by the lock lever 52 being retracted into the lock position, and in FIG. 2B the bias member 40 is extended to assist in moving the slide lock 44 back when the lock lever is released into an unlocked position.

FIG. 3 illustrates a disposable blade 2. The disposable blade includes a tip 4 connected to a mechanical enclosure 8. The tip 4 includes an angled portion 6, and the mechanical enclosure includes a blade module 70.

Figure 3B:
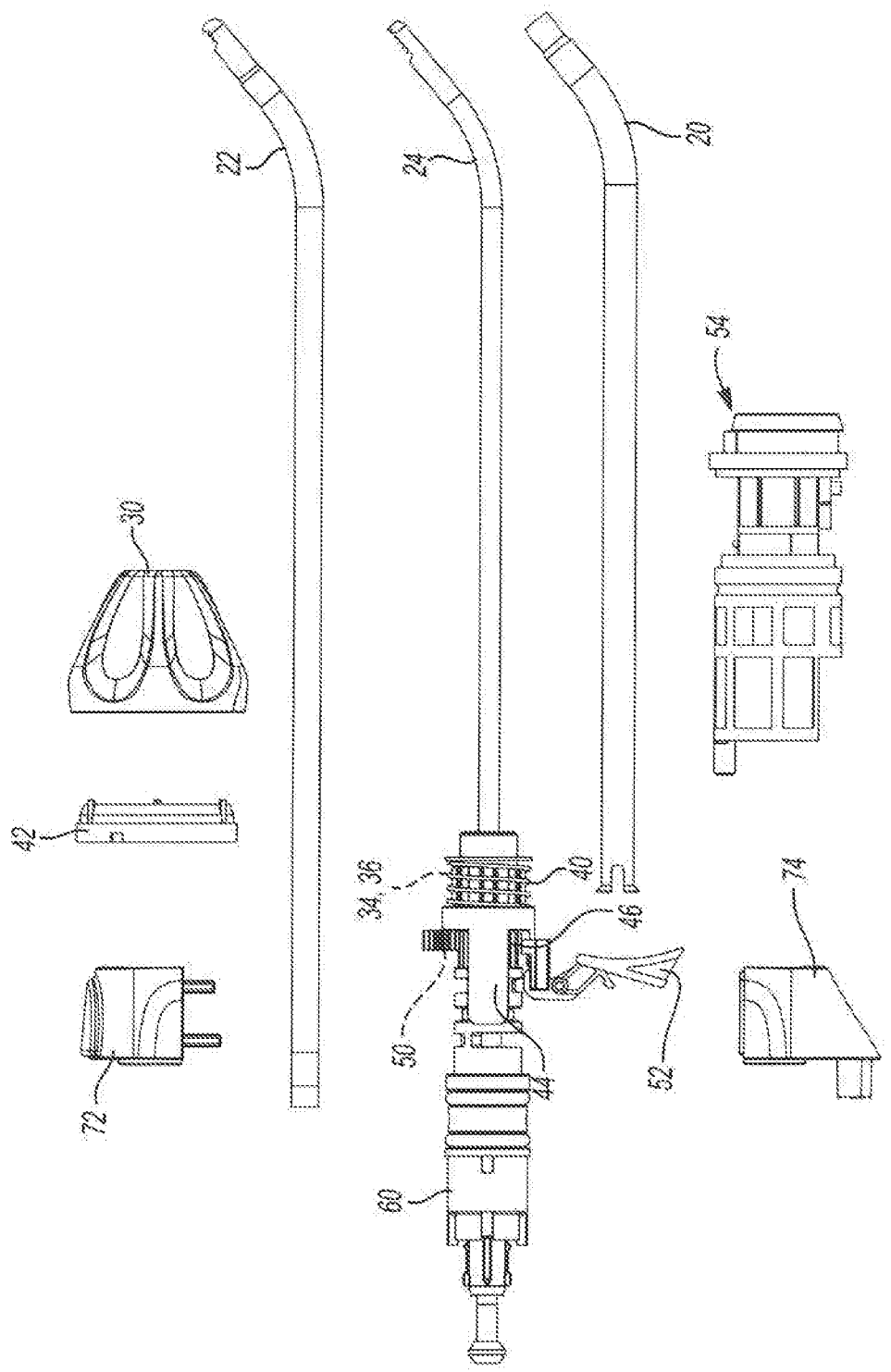
FIG. 3B illustrates an exploded view of one embodiment of the angled tip of FIG. 3 with the blade tip in an unlocked position.

FIGS. 3A and 3B illustrate an exploded view of the disposable blade of FIG. 3. The tip 4 comprises an outer tube 20, an intermediate tube 22, and an inner tube 24. The intermediate tube 22 includes a window 10 that exposes the inner tube 24. The tip 4 connects to the mechanical enclosure 8 by extending through the nosecone 30. The nosecone 30 includes a shim 32 (not shown) for axially spacing the locking spline 34 and biasing member 40 within the nosecone 30. A slide lock 44 is connected to a lock lever 52 by an actuation connection 46. The lock lever 52 is used to move the slide lock 44 between a locking position (as shown in FIG. 3A) and a non-locked position (as shown in FIG. 3B). When the lock lever 52 is moved to the lock position, the lock lever 52 pushes the slide lock 44 over the locking spline 34 so that ribs 36 on the locking spline 34 are engaged with teeth 48 (not shown) on the slide lock 44. When the lock lever 52 is in the locked position the tip 4 is locked in place so that the angled portion 6 of the tip points in a single direction. When the lock lever 52 is released the tip 4 can be rotated so that the angled portion 6 is adjusted and the angled portion can be angled towards a point of interest. A nosepiece gear 42 extends into the nosecone 30 and extends around the slide lock 44. During rotation of the nosepiece 30, the nosepiece gear 42 is rotated and the nosepiece gear 42 rotates a pair of pinion gears 50 so that a window 10 in intermediate tube 22 is directionally rotated towards a point of Interest. The window 10 can be rotated when the lock lever 52 is in the locked position (FIG. 3A) or the unlocked position (FIG. 3B). The pinion gears 50 are connected to a stationary collet 54. The collet 54 covers an outer hub 60 which rotates during operation of the disposable blade. A control enclosure 72 and a connection enclosure 74 form an enclosure behind the nosecone 30 and at least a portion of the slide lock 44 and assist in supporting the lock lever 52. At least a portion of the outer hub 60 extends beyond the control enclosure 72 and the connection enclosure 74. As is illustrated in FIG. 3A the bias member 40 is compressed by the lock lever 52 via the sliding lock 44 being retracted into the lock position, and in FIG. 3B the bias member 40 is extended to assist in moving the slide lock 44 back when the lock lever is released into an unlocked position.

Figure 4:
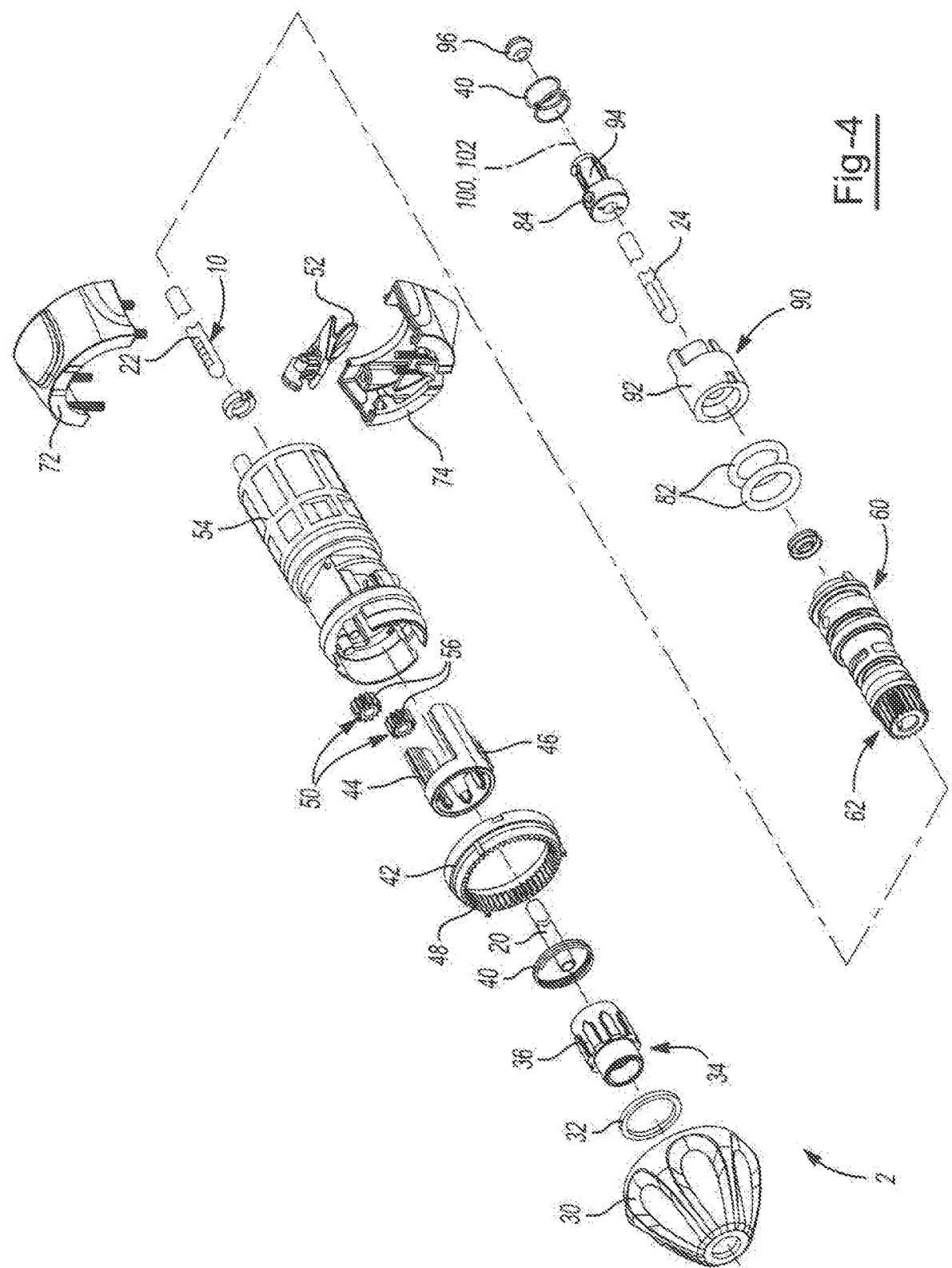
FIG. 4 illustrates an exploded view of a blade assembly having three tubes.

FIG. 4 is an exploded view illustrating additional features of a disposable blade 2. A nosecone 30 includes a shim 32, a locking spline 34 that has a plurality of ribs 36, and a biasing member 40. An outer tube 20 is connected to and extends through the locking spline 34. The biasing member 40 extends between the locking spline 34 and the slide lock 44 and assists in moving the slide lock 44. The slide lock 44 includes an actuation connection 46 that connects to a lock lever 52 that moves the slide lock 44. The slide lock 44 extends through a nosepiece gear 42 when the lock lever 52 is actuated from an unlocked position to a locked position so that the slide lock 44 slides over the locking spline 34. The nosepiece gear 42 has teeth 48 around an inside periphery that connect with teeth 56 of the pinion gears 50. The pinion gears 50 are connected to the collet 54 via a bearing surface, which connects to a handpiece (not shown) so that the collet 54 assists in fixedly connecting the disposable blade 2 to the handpiece. A portion of the collet 54 is surrounded by the control enclosure 72 and the connection enclosure 74. The connection enclosure 74 includes a hole (not shown) that the lock lever 52 extends through and locks unto so that the lock lever 52 maintains a locked position. An intermediate tube 22 including a window 10 extends through the collet 54, the slide lock 44, the locking spline 34, and the nosecone 30. The intermediate tube 22 is connected to the outer hub 60. The outer hub 60 includes a toothed portion 62 that is indirectly connected to the nosepiece 30. Rotational energy is transferred from the nosepiece 30 through the nosepiece gear 42 and the pinion gears 50 to the toothed portion 62 of the outer hub 60 so that the window 10 of the intermediate tube 22 is rotated to a direction of interest. A encapsulation connector 90 is connected to an end region of the outer hub 60. Two rings 82 are located on the outer hub 60 so that the connection to the collet 54 is sealed. The encapsulation connector 90 assists in holding the inner tube and includes two transmitters 92 that are in magnetic communication with two magnets 84 located in the inner hub 94 and a magnetic sensor (not shown) in the reusable handpiece. These, magnets in conjunction with software in a console, allows the user to toggle between an open and closed inner blade window regardless of the rotational position of the outermost window-carrying tube. The inner tube 24 extends into and through the encapsulation connector 90 and the intermediate tube 22. An end region of the inner tube 24 includes an inner hub 94 that connects the inner tube to coupler (not shown) that is connected to a motor (not shown) in a handpiece (not shown). The inner hub 94 extends at least partially into the encapsulation connector 90. The inner hub 94 includes a biasing member 40 and a coupling seal 96 so that the inner hub 94 is removably sealed and connected to a coupler of a handpiece. The outer tube 20, the intermediate tube 22, and the inner tube 24 extend along a common rotational axis 100. As illustrated, the rotational axis 100 of the tubes is also the longitudinal axis 102 of the locking spline 34.

Figure 5:
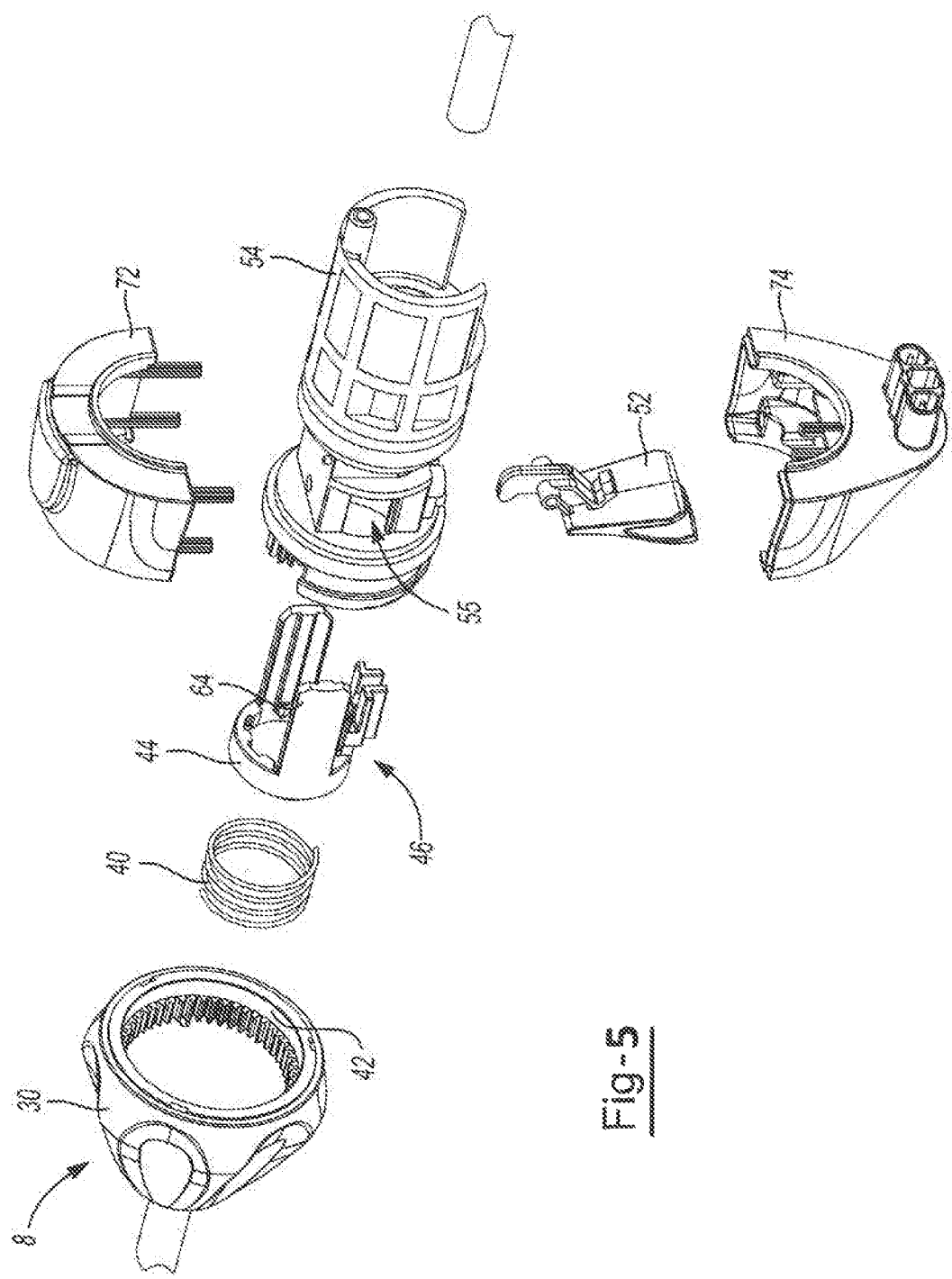
FIG. 5 illustrates an perspective view of an exploded mechanical enclosure.

FIG. 5 illustrates an exploded view of the mechanical enclosure 8. The enclosure 8 includes a control enclosure 72 and a connection enclosure 74 that surround a portion of the collet 54. The connection enclosure 74 includes a hole (not shown) so that the lock lever 52 can extend through and connect with the actuation connection 46 and move the slide lock 44. The slide lock 44 includes rails 64 that move along tracks 55 in the collet 54 so that the tracks 55 prevent rotational movement of the slide lock 44. The nosepiece gear 42 is connected to an end of the collet 54. The nosecone 30 houses the locking spline 34 which is covered by a biasing member 40 that assists in retracting the slide lock 44 when the lock lever 52 is moved from a locked position to an unlocked position.

Figure 6:
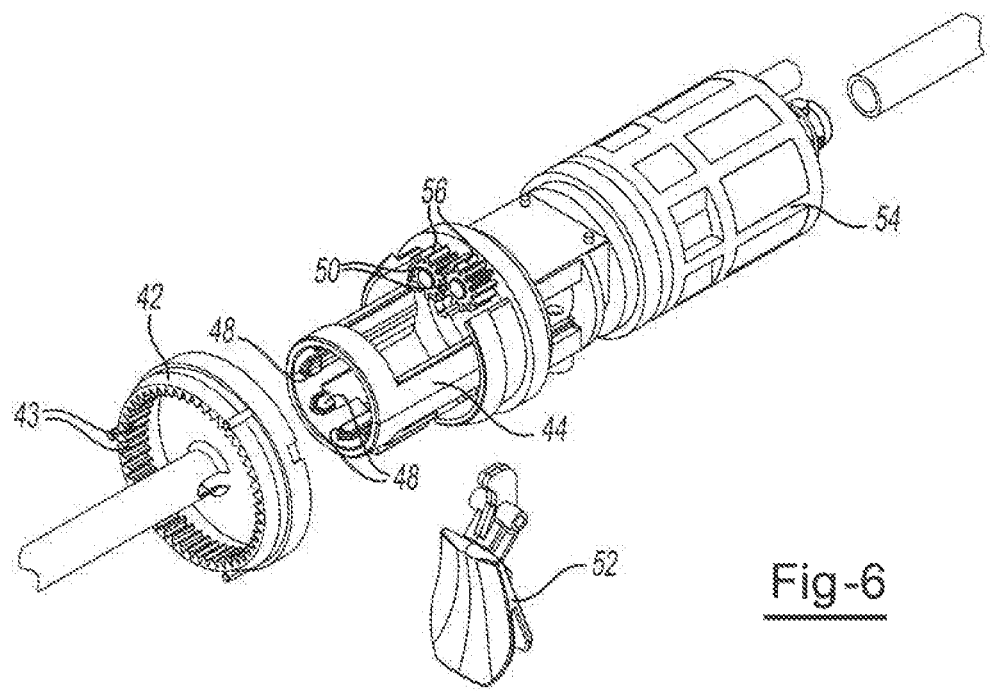
FIG. 6 illustrates a front perspective view of an exploded mechanical enclosure.

FIG. 6 illustrates the nosepiece gear 42. The nosepiece gear 42 includes teeth 43 around an inside periphery. The teeth 43 of the nosepiece gear 42 correlate to teeth 56 on the pinion gears 50 so that when the nosecone 30 (not shown) is rotated the nosepiece gear 42 rotates the pinion gears 50. The pinion gears 50 are connected to the collet 54 so that the pinion gears remain stationary. The slide lock 44 slides through the nosepiece gear 42 so that teeth 48 on the inside contact a locking spline 34 (not shown). The slide lock 44 is moved by a lock lever 52 that rests in a seat 76 of a control enclosure 72.

Figure 7:
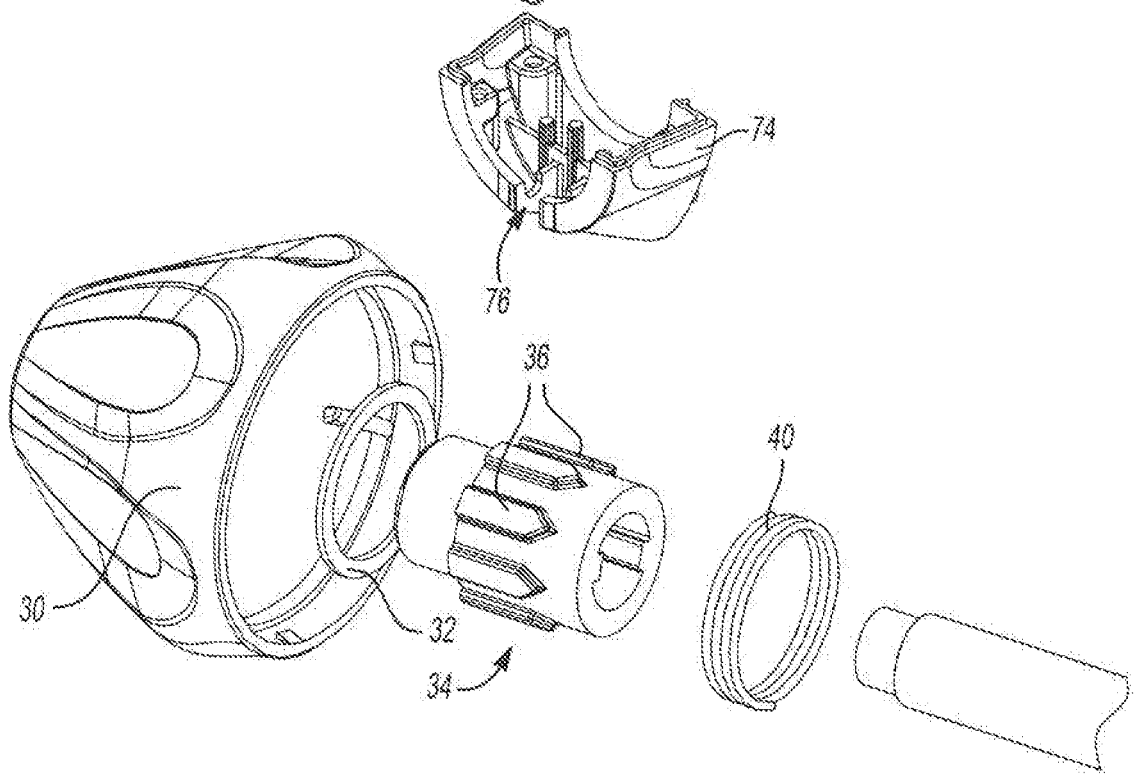
FIG. 7 illustrates an exploded view of a nosecone.

FIG. 7 illustrates an exploded view of the components of the nosecone 30. The nosecone 30 includes a shim 32 with a locking spine 34 connected to the nosecone 30. The locking spline 34 includes ribs 36 that form a fixed connection with a slide lock 44 (not shown). A bias member 40 fits between the slide lock 44 (not shown) and the shim 32 and assists in retracting the slide lock 44 (not shown).

Figure 8:
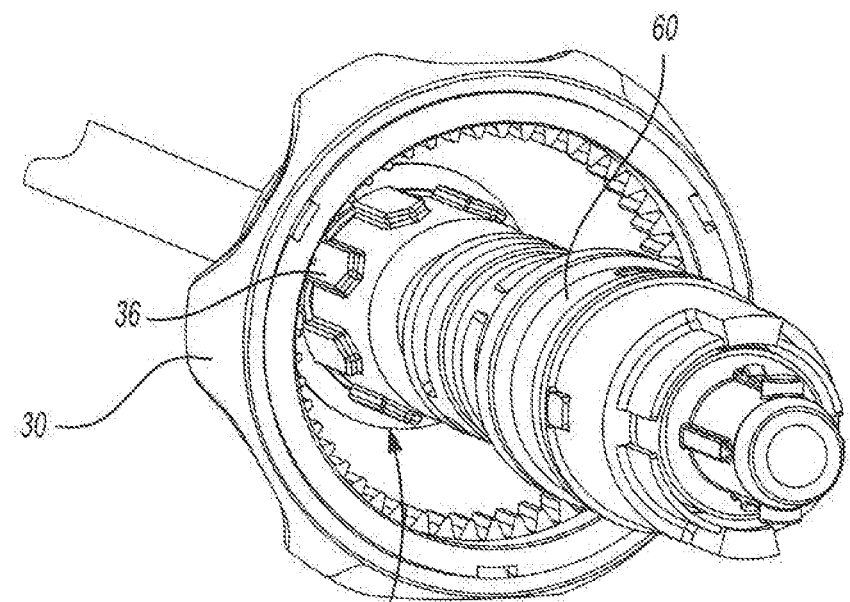
FIG. 8 illustrates a nosecone connected to an outer hub.

FIG. 8 illustrates the locking spline 34 connected to the nosecone 30. The locking spline 34 includes ribs 36. The outer hub 60 is free of a toothed portion and the area free of the toothed portion extends into the nosecone 30.

Figure 9:
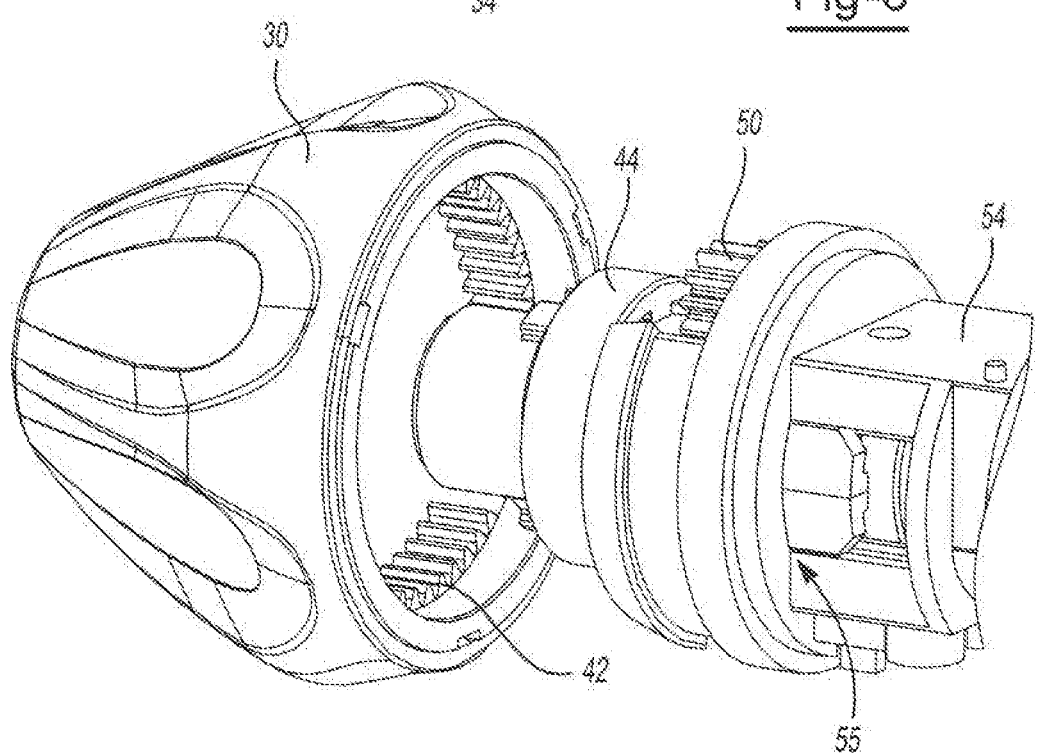
FIG. 9 illustrates a nosecone and collet.

FIG. 9 illustrates the nosepiece gear 42 fit into the nosecone 30. The slide lock 44 is extending from the collet 54. Pinion gears 50 are connected to the collet 54, and the track 55 extending along the longitudinal axis of the collet 54.

Figure 10:
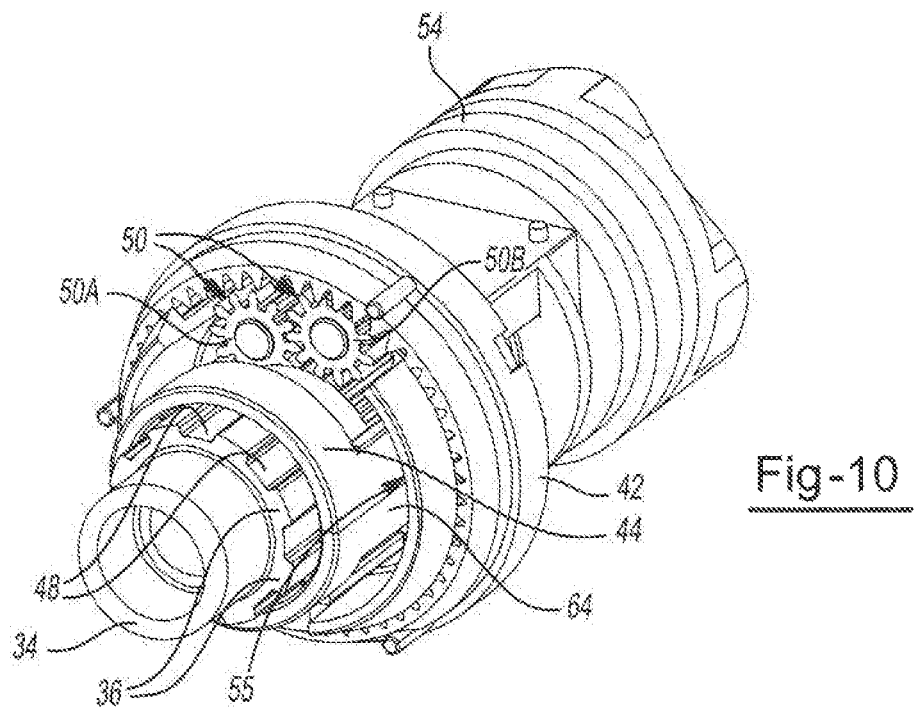
FIG. 10 illustrates a perspective view of a collet.

FIG. 10 illustrates the collet 54 supporting the pinion gears 50. The pinion gears 50 are offset so that pinion gear 50B forms a rotational connection with nosepiece gear 42. Pinion gear 50B forms a connection with pinion gear 50A so that rotational forces are transferred between pinion gear 50A and 50B. Pinion gear 50A forms a rotational connection with the toothed portion 62 of the outer hub 60 so that a rotational force is transferred from the pinion gear 50A to the outer hub 60. A user rotates an window 10 (not shown) by rotating a nosecone 30 (not shown) that rotates the nosepiece gear 42, the nosepiece gear 42 rotates the pinion gear 50B and the pinion gear 50B rotates the pinion gear 50A, which then rotates the outer hub 60, which rotates a window 10 (not shown). The slide lock 44 extends partially out of the collet 54 so that the rails 64 of the slide lock 44 are extended into the tracks 55 in the collet 54 and rotational movement of the slide lock 44 is prevented. The slide lock 44 includes teeth 48 for connecting to ribs 36 on the locking spline 34.

Figure 11:
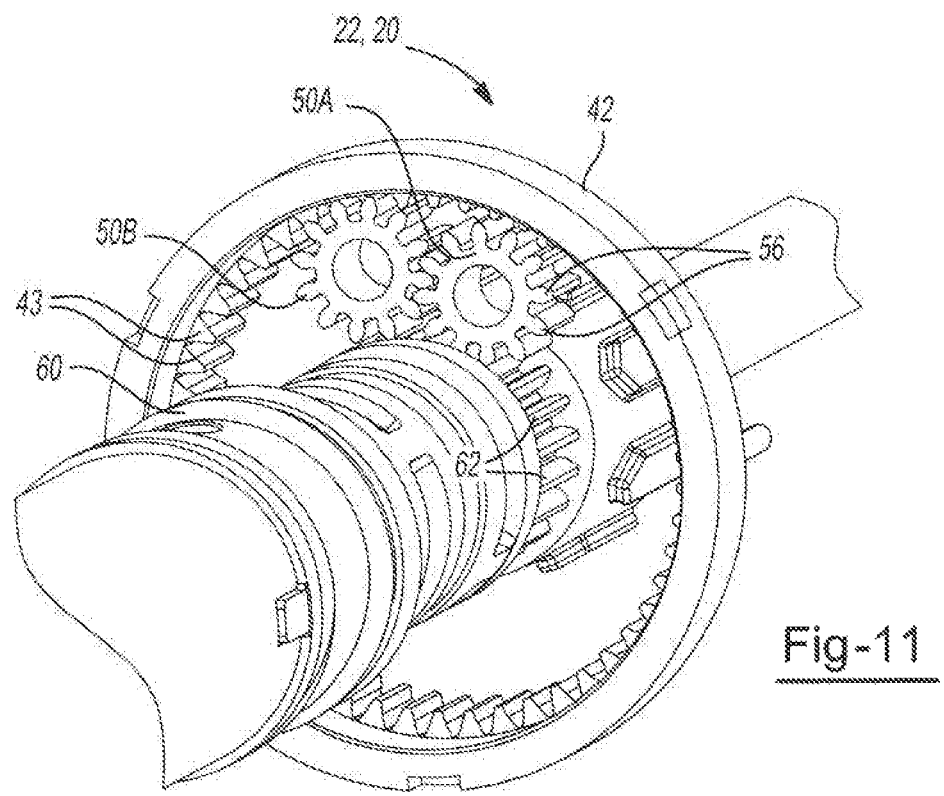
FIG. 11 illustrates a perspective view of the tears of the teachings herein.

FIG. 11 illustrates the connections of each of the rotational components so that a window 10 (not shown) can be rotated to a point of interest. The outer hub 60 has a toothed portion 62 that extends into a nosepiece gear 42 and into contact with one of the two pinion gears 50A and 50B. When a nosecone 30 (not shown) is rotated the rotational forces are transferred to the nosepiece gear 42. The nosepiece gear 42 includes teeth 43 that rotate and transfer the rotational energy to the teeth 56 of the first pinion gears 50A. The first pinion gear 50A teeth 56 transfer the rotational energy to the second pinion gear 50B. The teeth 56 of the second pinion gear 50B are in rotational connection with the toothed portion 62 of the rotary outer hub 60 that is connected to the intermediate tube 22 in a three tube system or the outer tube 20 in a two tube system. The teeth 56 on the first pinion gear 50A are free of direct communication (i.e., include a clearance) with the toothed portion 62 of the inner hub 60. The teeth 56 on the second pinion gear 50B are free of direction communication (i.e., include a clearance) with the teeth 43 on the nosepiece gear 42.

Figure 12:
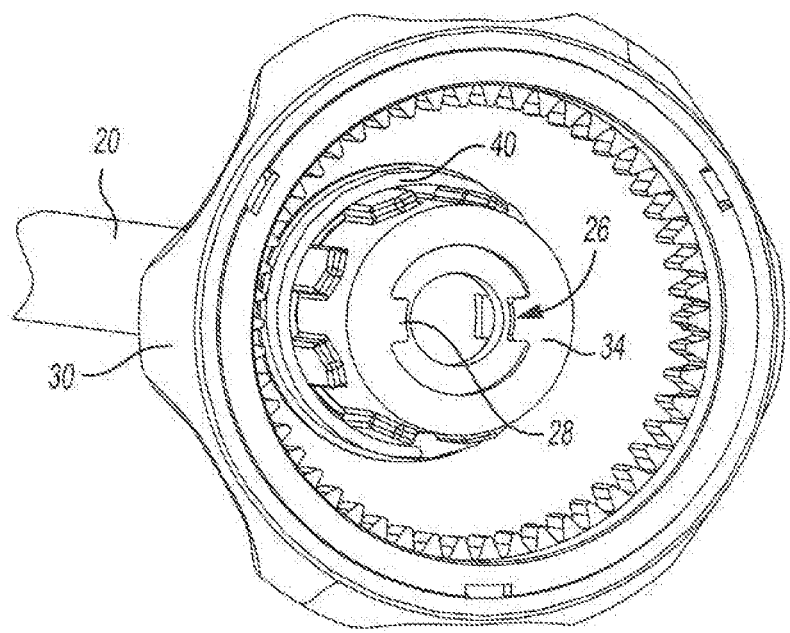
FIG. 12 illustrates a nosecone.

FIG. 12 illustrates the nosecone 30 including a biasing member 40 and the locking spline 34. The locking spline 34 is connected to an end of the outer tube 20. The end of the outer tube 20 includes slots 26 that fit with corresponding tabs 28 in the locking spline 34 so that rotation of the outer tube 20 is prevented when in the lock lever (not shown) is in the locked position.

Figure 13:
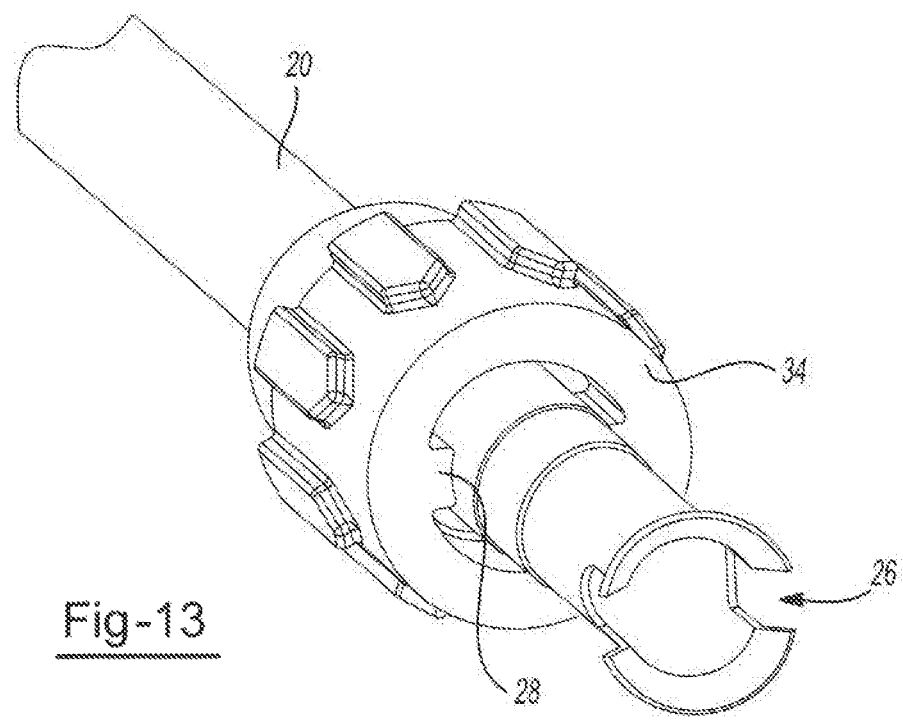
FIG. 13 illustrates a locking spline.

FIG. 13 illustrates the locking spline 34 extended down the outer tube 20 so that an end of the outer tube 20 is exposed. The outer tube 20 includes slots 26 that couple to tabs 28 of the locking spline 34 so that movement of the outer tube 20 is prevented when the device is locked.

Figure 14:
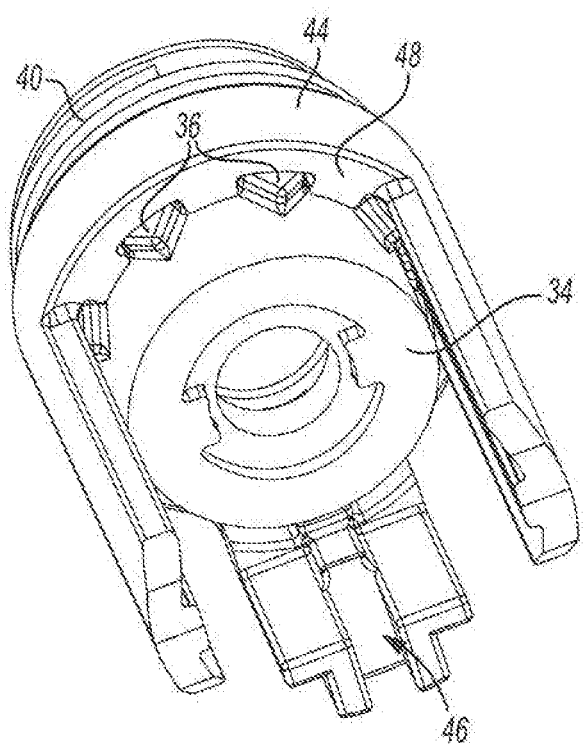
FIG. 14 illustrates a locking spline and slide lock.

FIG. 14 illustrates the slide lock 44 connected to the locking spline 34. The ribs 36 of the locking spline 34 are tapered so that the teeth 48 of the slide lock 44 slides into a fixed connection when the device is locked. The slide lock 44 compresses the bias member 40. The slide lock 44 includes an actuation connection 46 that couples to the lock lever 52 (not shown) for moving the slide lock 44.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus. "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including"

to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A blade assembly comprising:
   a. a tip including two or more tubes, wherein the two or more tubes include at least:
      i. an outer tube and
      ii. an inner tube; and
   b. a mechanical enclosure including:
      i. a locking spline having a longitudinal axis; and
      ii. a slide lock that is movable between a locked position and an unlocked position within the mechanical enclosure;
      wherein the slide lock moves between the locked position and the unlocked position along the longitudinal axis of the locking spline, and the slide lock in the locked position extends over the locking spline forming a locked state where the locking spline is located within the slide lock so that rotational movement of the locking spline, around the longitudinal axis of the locking spline, is prevented; and
      wherein the outer tube is coupled to the locking spline so that rotational movement of the outer tube, around the longitudinal axis of the locking spline, is prevented during the locked state.

2. The blade assembly of claim 1, wherein the slide lock includes an actuation connection that connects the slide lock to a lock lever that moves the slide lock between the locked position and the unlocked position.

3. The blade assembly of claim 1, wherein the mechanical enclosure includes a control enclosure and a connection enclosure that at least partially cover the slide lock.

4. The blade assembly of claim 3, wherein a lock lever extends through the connection enclosure so that the lock lever is exposed for actuation by a user, and the lock lever moves the slide lock between the locked position and the unlocked position.

5. The blade assembly of claim 1, wherein at least one of the two or more tubes extend through the slide lock, and wherein the outer tube includes slots.

6. The blade assembly of claim 5, wherein the locking spline includes tabs that correspond to the slots in the outer tube so that the outer tube and the locking spline form a fixed connection.

7. The blade assembly of claim 1, wherein the locking spline includes one or more ribs, and wherein the slide lock includes one or more teeth, and wherein the one or more ribs are tapered at one end.

8. The blade assembly of claim 7, wherein the one or more teeth correspond with the one or more ribs of the locking spline so that when the slide lock slides over the locking spline in the locked state the one or more ribs and the one or more teeth form a fixed connection and prevent rotation of the outer tube, the locking spline, or both.

9. The blade assembly of claim 1, wherein the slide lock is housed in a collet, and the collet extends into a handpiece and assists in connecting the blade assembly to the handpiece.

10. The blade assembly of claim 9, wherein the collet is fixed to the handpiece so that the collet is free of rotational movement, lateral movement, longitudinal movement, or a combination thereof.

11. The blade assembly of claim 1, wherein the at least two tubes of the tip are three tubes, and the outer tube is a rigid sheath that forms a bend so that an intermediate tube and the inner tube located within the outer tube are bent at an angle.

12. The blade assembly of claim 1, wherein a biasing member is located between the locking spline and the slide lock and the biasing member assists in moving the slide lock between the locked position and the unlocked position.

13. The blade assembly of claim 1, wherein the locking spline is connected to a nosecone.

14. The blade assembly of claim 1, wherein the blade assembly includes a nosecone and the locking spline and the nosecone are separated by a shim.

15. A blade assembly comprising:
   a. a tip including three or more tubes, wherein the three or more tubes include at least:
      i. an outer tube;
      ii. an inner tube; and
      iii. an intermediate tube located at least partially between the inner tube and the outer tube; and
   b. a mechanical enclosure including:
      i. a nosecone located distal to a collet and the three or more tubes extending distal of the nosecone, the nosecone including a nosepiece gear;
      ii. the collet having one or more pinion gears that are in communication with the nosepiece gear;
      wherein the intermediate tube is connected to an outer hub that extends though the collet, the outer hub including a toothed portion that is in communication with the one or more pinion gears so that rotation of the nosecone causes rotation of the intermediate tube relative to the outer tube;
      wherein the outer tube is connected to a locking spline, and the locking spline assists in preventing rotation of the outer tube.

16. The blade assembly of claim 15, wherein the one or more pinion gears are two pinion gears so that the intermediate tube rotates in the same direction as the nosecone.

17. The blade assembly of claim 15, wherein the intermediate tube includes a window that exposes at least a portion of the inner tube, and wherein the inner tube rotates independently of the intermediate tube, the outer tube, or both.

18. The blade assembly of claim 15, wherein the nosecone and the nosepiece gear are two pieces or the nosepiece gear is integrally formed in the nosecone.

19. The blade assembly of claim 15, wherein the blade assembly includes a slide lock and rotation of the locking spline is prevented when the slide lock is moved from an unlocked position to a locked position.

\* \* \* \* \*